United States Patent
Markovitz et al.

(10) Patent No.: US 10,450,355 B2
(45) Date of Patent: Oct. 22, 2019

(54) LECTINS AND USES THEREOF

(71) Applicant: THE REGENTS OF THE UNIVERSITY OF MICHIGAN, Ann Arbor, MI (US)

(72) Inventors: David M. Markovitz, Ann Arbor, MI (US); Jeanne A. Stuckey, Fenton, MI (US); Daniel M. Boudreaux, Frederick, MD (US); Jennifer Meagher, Plymouth, MI (US); Hashim Al-Hashimi, Chapel Hill, NC (US); Loic Salmon, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/511,554

(22) PCT Filed: Sep. 16, 2015

(86) PCT No.: PCT/US2015/050383
§ 371 (c)(1),
(2) Date: Mar. 15, 2017

(87) PCT Pub. No.: WO2016/044397
PCT Pub. Date: Mar. 24, 2016

(65) Prior Publication Data
US 2017/0291928 A1 Oct. 12, 2017

Related U.S. Application Data

(60) Provisional application No. 62/051,081, filed on Sep. 16, 2014.

(51) Int. Cl.
*C07K 14/42* (2006.01)
*A61L 31/16* (2006.01)
*A61K 38/16* (2006.01)
*A61K 38/17* (2006.01)
*A61L 31/04* (2006.01)
*A61K 9/00* (2006.01)
*A61K 38/00* (2006.01)

(52) U.S. Cl.
CPC ............ *C07K 14/42* (2013.01); *A61K 38/168* (2013.01); *A61K 38/1732* (2013.01); *A61L 31/047* (2013.01); *A61L 31/16* (2013.01); *A61K 9/0034* (2013.01); *A61K 38/00* (2013.01); *A61L 2300/404* (2013.01); *A61L 2300/408* (2013.01)

(58) Field of Classification Search
CPC .............................. C07K 14/42; A61K 38/168
See application file for complete search history.

(56) References Cited

U.S. PATENT DOCUMENTS

2008/0148432 A1* 6/2008 Abad .................. C07K 14/415 800/279
2013/0096051 A1* 4/2013 Markovitz ............ C07K 14/42 514/2.4

FOREIGN PATENT DOCUMENTS

WO 2016044397 A1 3/2016

OTHER PUBLICATIONS

Liao, The multiple roles of histidine in protein interactions, Chemistry Central Journal 2013, 7:44 (Year: 2013).*
Raval, A database analysis of jacalin-like lectins: sequence—structure—function relationships, Glycobiology 2004, vol. 14 No. 12 ( Year: 2004).*
Wimmerova, Stacking Interactions between Carbohydrate and Protein Quantified by Combination of Theoretical and Experimental Methods, PloS One 2012, vol. 7, Issue 10 (Year: 2012).*
GenBank: ADW77219.1 (Year: 2010).*
Raval, A database analysis of jacalin-like lectins: sequence—structure—function relationships, Glycobiology 2004, vol. 14 No. 12, of record (Year: 2004).*
GenBank: ADW77219.1 (Year: 2013).*
Liao (The multiple roles of histidine in protein interactions, Chemistry Central Journal 2013, 7:44, of record) (Year: 2013).*
André et al., "First demonstration of differential inhibition of lectin binding by synthetic tri- and tetravalent glycoclusters from cross-coupling of rigidified 2-propynyl lactoside." Org Biomol Chem. Nov. 21, 2003;1(22):3909-16.
André et al., "Glycocluster design for improved avidity and selectivity in blocking human lectin/plant toxin binding to glycoproteins and cells." Mol Pharm. Dec. 6, 2010;7(6):2270-9.
André et al., "Lactose-containing starburst dendrimers: influence of dendrimer generation and binding-site orientation of receptors (plant/animal lectins and immunoglobulins) on binding properties." Glycobiology. Nov. 1999;9(11):1253-61.
André et al., "Phenylenediamine-based bivalent glycocyclophanes: synthesis and analysis of the influence of scaffold rigidity and ligand spacing on lectin binding in cell systems with different glycomic profiles." Org Biomol Chem. Nov. 21, 2009;7(22):4715-25.
Bricogne G., 2011.
Chabre et al., "The Chemist's Way to Prepare Multivalency" WILEY-VCH Verlag GmbH & Co. KGaA, Weinheim 2009, pp. 53-70.

(Continued)

*Primary Examiner* — Karlheinz R. Skowronek
*Assistant Examiner* — Khalid Kader
(74) *Attorney, Agent, or Firm* — Casimir Jones, S.C.; Tanya Arenson

(57) ABSTRACT

Provided herein are chemical compounds, methods for their discovery, and their therapeutic and research use. Further provided herein are antiviral and antimicrobial lectin compounds and methods of their use.

15 Claims, 22 Drawing Sheets

Specification includes a Sequence Listing.

(56) References Cited

OTHER PUBLICATIONS

Chabre et al., "Design and creativity in synthesis of multivalent neoglycoconjugates." Adv Carbohydr Chem Biochem. 2010;63:165-393.

Chen et al., "MolProbity: all-atom structure validation for macromolecular crystallography." Acta Crystallogr D Biol Crystallogr. Jan. 2010;66(Pt 1):12-21.

Clavel et al., "NMR Investigation of the Bound Conformation of Natural and Synthetic Oligomannosides to Banana Lectin" 2007 Eur J Org Chem, 1577-1585.

Collins at el., "Purification of the influenza hemagglutinin glycoprotein and characterization of its carbohydrate components." J Virol. May 1978;26(2):457-67.

Denton et al., "Generation of HIV latency in humanized BLT mice." J Virol. Jan. 2012;86(1):630-4.

Emsley et al., "Features and development of Coot." Acta Crystallogr D Biol Crystallogr. Apr. 2010;66(Pt 4):486-501.

Férir et al., "Synergistic in vitro anti-HIV type 1 activity of tenofovir with carbohydrate-binding agents (CBAs)." Antiviral Res. Jun. 2011;90(3):200-4.

Gabius et al., "Endogenous sugar-binding proteins in human breast tissue and benign and malignant breast lesions." Cancer. Mar. 15, 1988;61(6):1125-31.

Gabius et al., "Glycohistochemistry: the why and how of detection and localization of endogenous lectins." Anat Histol Embryol. Feb. 2001;30(1):3-31.

Gavrovic-Jankulovic et al., "A novel recombinantly produced banana lectin isoform is a valuable tool for glycoproteomics and a potent modulator of the proliferation response in CD3+, CD4+, and CD8+ populations of human PBMCs." Int J Biochem Cell Biol. 2008;40(5):929-41.

Hooft et al., "Errors in protein structures." Nature. May 23, 1996;381(6580):272.

Kjaergaard et al., "Sequence correction of random coil chemical shifts: correlation between neighbor correction factors and changes in the Ramachandran distribution." J Biomol NMR. Jun. 2011;50(2):157-65.

Kleywegt et al., "The Uppsala Electron-Density Server." Acta Crystallogr D Biol Crystallogr. Dec. 2004;60(Pt 12 Pt 1):2240-9.

Kopitz et al., "Single-site mutational engineering and following monoPEGylation of the human lectin galectin-2: effects on ligand binding, functional aspects, and clearance from serum." Mol Pharm. May 6, 2013;10(5):2054-61.

Li et al., "Internal dynamics control activation and activity of the autoinhibited Vav DH domain." Nat Struct Mol Biol. Jun. 2008;15(6):613-8.

Liao et al., "The multiple roles of histidine in protein interactions." Chem Cent J. Mar. 1, 2013;7(1):44., 1-12.

McBroom et al., "[16] Carbohydrate antigens: Coupling of carbohydrates to proteins by diazonium and phenylisothiocyanate reactions" Methods in Enzymology, vol. 28, 1972, pp. 212-219.

McCoy et al., "Phaser crystallographic software." J Appl Crystallogr. Aug. 1, 2007;40(Pt 4):658-674.

Meagher et al., "Crystal structure of banana lectin reveals a novel second sugar binding site." Glycobiology. Oct. 2005;15(10):1033-42.

Murphy et al., "The third dimension of reading the sugar code by lectins: design of glycoclusters with cyclic scaffolds as tools with the aim to define correlations between spatial presentation and activity." Molecules. Apr. 4, 2013;18(4):4026-53.

Nakamura-Tsuruta et al., "Analysis of the sugar-binding specificity of mannose-binding-type Jacalin-related lectins by frontal affinity chromatography—an approach to functional classification." FEBS J. Mar. 2008;275(6):1227-39.

Ng et al., "Soluble host defense lectins in innate immunity to influenza virus." J Biomed Biotechnol. 2012;2012:732191.

Otwinowski et al., "[20] Processing of X-ray diffraction data collected in oscillation mode."Methods Enzymol. 1997;276:307-326.

Palmer et al., "NMR characterization of the dynamics of biomacromolecules." Chem Rev. Aug. 2004;104(8):3623-40.

Papadopoulos et al., "Diazo transfer and click chemistry in the solid phase syntheses of lysine-based glycodendrimers as antagonists against *Escherichia coli* FimH." Mol Pharm. Mar. 5, 2012;9(3):394-403.

Percec et al., "Modular synthesis of amphiphilic Janus glycodendrimers and their self-assembly into glycodendrimersomes and other complex architectures with bioactivity to biomedically relevant lectins." J Am Chem Soc. Jun. 19, 2013;135(24):9055-77.

Raval et al., "A database analysis of jacalin-like lectins: sequence—structure—function relationships." Glycobiology. Dec. 2004;14(12):1247-63.

Reading et al., "Involvement of the mannose receptor in infection of macrophages by influenza virus." J Virol. Jun. 2000;74(11):5190-7.

Sattler et al., "Heteronuclear multidimensional NMR experiments for the structure determination of proteins in solution." 1999 Prog NMR Spectrosc 34, 93-158.

Singh et al., "Unusual sugar specificity of banana lectin from Musa paradisiaca and its probable evolutionary origin. Crystallographic and modelling studies." Glycobiology. Oct. 2005;15(10):1025-32.

Swanson et al., "A lectin isolated from bananas is a potent inhibitor of HIV replication." J Biol Chem. Mar. 19, 2010;285(12):8646-55.

Temperton et al., "A sensitive retroviral pseudotype assay for influenza H5N1-neutralizing antibodies." Influenza Other Respir Viruses. May 2007;1(3):105-12.

Van Demme et al., "Isolation and characterization of a lectin with exclusive specificity towards mannose from snowdrop (*Galanthusnivalis*) bulbs" Febs Lett 215, 1987, p. 140-144.

Wahl et al., "Human breast milk and antiretrovirals dramatically reduce oral HIV-1 transmission in BLT humanized mice." PLoS Pathog. 2012;8(6):e1002732.

Winn et al., "Macromolecular TLS refinement in REFMAC at moderate resolutions." Methods Enzymol. 2003;374:300-21.

Tucker et al., "Validation of crystallographic models containing TLS or other descriptions of anisotropy." Acta Crystallogr D Biol Crystallogr. Aug. 2010;66(Pt 8):889-900.

International Search Report of corresponding PCT/US2015/050383 18 pages, dated Jan. 22, 2016.

* cited by examiner

Figure 14 gb|ADW77219.1| lectin [Musa acuminata AAA Group](SEQ ID NO:2)

Sequence:
```
Musa      MNGAIKVGAWGGNGGSAFDMGPAHRIISVKIYSGDVVDGVDVTFTSYEKTETRHFGGSGG    60
Musa      TPHEIVLQEGEYLVGMTGEFAN  GVVVVGKLGFNTNKKSYGPFGNTGGTPFSLPIVAGK   120
Musa      ISGFFGRGGQFLDAIGVYLEP   141
```

Sequence Alignment with Banlec (SEQ ID NO:9) highlighting the 2 hyrophobic residues in the loop:
```
BanLec    MNGAIKVGAWGGNGGSAFDMGPAYRIISVKIFSGDVVDGVDVTFTYYGKTETRHYGGSGG    60
(SEQ ID NO:9)
          MNGAIKVGAWGGNGGSAFDMGPA+RIISVKI+SGDVVDGVDVTFT Y KTETRH+GGSGG
Musa      MNGAIKVGAWGGNGGSAFDMGPAHRIISVKIYSGDVVDGVDVTFTSYEKTETRHFGGSGG    60

BanLec    TPHEIVLQEGEYLVGMAGEVAN  GAVVLGKLGFSTNKKAYGPFGNTGGTPFSLPIAAGK   120
          TPHEIVLQEGEYLVGM GE AN  G VV+GKLGF+TNKK+YGPFGNTGGTPFSLPI AGK
Musa      TPHEIVLQEGEYLVGMTGEFAN  GVVVVGKLGFNTNKKSYGPFGNTGGTPFSLPIVAGK   120

BanLec    ISGFFGRGGKFLDAIGVYLEP   141
          ISGFFGRGG+FLDAIGVYLEP
Musa      ISGFFGRGGQFLDAIGVYLEP   141
``` gb|EAY82651.1| hypothetical protein OsI_37872 [Oryza sativa Indica Group] (SEQ ID NO:3)

Sequence:
```
Oryza     KVGPWGGNGGTPQDITETPKRLESITIRSGEVVDSISFSYFDQAGQKRVAGPWGGPGGNL   223
Oryza     NTIELSSSEFLKEVSGTFGT  GSNVITSIKFVTNVKTYGPFGKQNGTPFSIPVQNNSSV   283
Oryza     VGFFGRGGKYLDAVGVYVHP    303
```

Sequence Alignment with Banlec(SEQ ID NO:9)highlighting the 2 hyrophobic residues in the loop:
```
BanLec    KVGAWGGNGGSAFDMGPAY-RIISVKIFSGDVVDGVDVTFTY--YGKTETRHYGGSGGTP    62
          KVG WGGNGG+   D+      R+ S+ I SG+VVD +       K      +GG GG
Oryza     KVGPWGGNGGTPQDITETPKRLESITIRSGEVVDSISFSYFDQAGQKRVAGPWGGPGGNL   223

BanLec    HEIVLQEGEYLVGMAGEVAN  GAVVLGKLGFSTNKKAYGPFGNTGGTPFSLPIAAG-KI   121
          + I L   E+L  ++G     G+ V+  + F TN K YGPFG   GTPFS+P+     +
Oryza     NTIELSSSEFLKEVSGTFGT  GSNVITSIKFVTNVKTYGPFGKQNGTPFSIPVQNNSSV   283

BanLec    SGFFGRGGKFLDAIGVYLEP    141
           GFFGRGGK+LDA+GVY+ P
Oryza     VGFFGRGGKYLDAVGVYVHP    303
```

Figure 14 Cont.

```
dbj|BAG24500.1| jacalin-related lectin [Cycas rumphii] (SEQ ID NO:4)

Sequence:
C.rumphii  GVGKEGPYGGVGGAPWDDGPQFGISRILIHSGDVVDSIQVDHR-------PKHGGPGGTA  204
C.rumphii  TEIQFDPDEVLKKIEGYFGPXXGRPSIIKSLTIHTNLTKYGPFGTAGGTQGDVHFASTSL  264

C.rumphii  EHGKIVGFFGRAAEYLDAIGVYIA  288

Sequence Alignment with Banlec highlighting the 2 hyrophobic residues in the
loop:
BanLec     GAIKVGAWGGNGGSAFDMGPAYRIISVKIFSGDVVDGVDVTFTYYGKTETRHYGGSGGTP  62
           G  K G +GG GG+ +D GP + I  + I SGDVVD + V           +GG GGT
C.rumphii  GVGKEGPYGGVGGAPWDDGPQFGISRILIHSGDVVDSIQVDHR-------PKHGGPGGTA  204

BanLec     HEIVLQEGEYLVGMAGEVANXXGAV-VLGKLGFSTNKKAYGPFGNTGGT-----PFSLPI  116
           EI    E L + G    XXG   ++ L    TN   YGPFG GGT        S   +
C.rumphii  TEIQFDPDEVLKKIEGYFGPXXGRPSIIKSLTIHTNLTKYGPFGTAGGTQGDVHFASTSL  264

BanLec     AAGKISGFFGRGGKFLDAIGVYLE  140
              GKI GFFGR   ++LDAIGVY+
C.rumphii  EHGKIVGFFGRAAEYLDAIGVYIA  288
```

---

```
dbj|BAE95375.1| lectin [Cycas revoluta] (SEQ ID NO:5)

Sequence:
C.rev  GVGKEGPYGGVGGAPWDDGPQFGISRILIHSGDVVDSIQVDHR-------PKHGGPGGAA  204
C.rev  TEIQFNPDEVLKKIEGYFGPXXGRPSIIKSLTFHTNLTKYGPFGTAGGTQGDVHFASTSL  264
C.rev  EHGKIVGFFGRAAQYLDAIGVYIA  288

Sequence Alignment with Banlec(SEQ ID NO:9)highlighting the 2 hyrophobic
residues in the loop:
BanLec  GAIKVGAWGGNGGSAFDMGPAYRIISVKIFSGDVVDGVDVTFTYYGKTETRHYGGSGGTP  62
        G  K G +GG GG+ +D GP + I  + I SGDVVD + V           +GG GG
C.rev   GVGKEGPYGGVGGAPWDDGPQFGISRILIHSGDVVDSIQVDHR-------PKHGGPGGAA  204

BanLec  HEIVLQEGEYLVGMAGEVANXXGAV-VLGKLGFSTNKKAYGPFGNTGGT-----PFSLPI  116
        EI    E L + G    XXG   ++ L F TN   YGPFG GGT        S   +
C.rev   TEIQFNPDEVLKKIEGYFGPXXGRPSIIKSLTFHTNLTKYGPFGTAGGTQGDVHFASTSL  264

BanLec  AAGKISGFFGRGGKFLDAIGVYLE  140
           GKI GFFGR   ++LDAIGVY+

C.rev   EHGKIVGFFGRAAQYLDAIGVYIA  288
```

Figure 14 Cont.

ref|XP_004979669.1| PREDICTED: mannose/glucose-specific lectin-like isoform
X1 [Setari 4714 italica] (SEQ ID NO:6)

```
Sequence:
Set X1    GVARIGPWGGDRGVLHDITVTPHHLERVTIFSGTIIDSLEFLYSDHDGKQHTAGPWGGCG    758
Set X1    GGGRKIRFDPSEFIVKVSGTFCAWWGVKNVLSSLTLVTNTGRSYGPYGTEFGTAFHVPEQ    818
Set X1    SNSRIVGFFAHGEDYIEAIGAYVRT    843
```

Sequence Alignment with Banlec (SEQ ID NO:9) highlighting the 2 hyrophobic
residues in the loop:
```
BanLec    GAIKVGAWGGNGGSAFDMGPAYR-IISVKIFSGDVVDGVDVTF--TYYGKTETRHYGGSG    59
          G  ++G WGG+  G    D+        +  V IFSG ++D ++  +      +   +GG G
Set X1    GVARIGPWGGDRGVLHDITVTPHHLERVTIFSGTIIDSLEFLYSDHDGKQHTAGPWGGCG    758

BanLec    GTPHEIVLQEGEYLVGMAGEVANWWGA-VVLGKLGFSTNKKA-YGPFGNTGGTPFSLPIA    117
          G   +I     E++V ++G    WWG   VL  L   TN      YGP+G   GT F +P
Set X1    GGGRKIRFDPSEFIVKVSGTFCAWWGVKNVLSSLTLVTNTGRSYGPYGTEFGTAFHVPEQ    818

BanLec    AG-KISGFFGRGGKFLDAIGVYLEP    141
          +   +I GFF  G   +++AIG Y+
Set X1    SNSRIVGFFAHGEDYIEAIGAYVRT    843
``` ref|XP_004979670.1| PREDICTED: mannose/glucose-specific lectin-like isoform
X2 [Setaria 4714 italica] (SEQ ID NO:7)

```
Sequence:
Set X2    GVARIGPWGGDRGVLHDITVTPHHLERVTIFSGTIIDSLEFLYSDHDGKQHTAGPWGGCG    737
Set X2    GGGRKIRFDPSEFIVKVSGTFCAWWGVKNVLSSLTLVTNTGRSYGPYGTEFGTAFHVPEQ    797
Set X2    SNSRIVGFFAHGEDYIEAIGAYVRT    822
```

Sequence Alignment with Banlec highlighting the 2 hyrophobic residues in the
loop:
```
BanLec    GAIKVGAWGGNGGSAFDMGPAYR-IISVKIFSGDVVDGVDVTF--TYYGKTETRHYGGSG    59
          G  ++G WGG+  G    D+        +  V IFSG ++D ++  +      +   +GG G
Set X2    GVARIGPWGGDRGVLHDITVTPHHLERVTIFSGTIIDSLEFLYSDHDGKQHTAGPWGGCG    737

BanLec    GTPHEIVLQEGEYLVGMAGEVANWWGA-VVLGKLGFSTNKKA-YGPFGNTGGTPFSLPIA    117
          G   +I     E++V ++G    WWG   VL  L   TN      YGP+G   GT F +P
Set X2    GGGRKIRFDPSEFIVKVSGTFCAWWGVKNVLSSLTLVTNTGRSYGPYGTEFGTAFHVPEQ    797

BanLec    AG-KISGFFGRGGKFLDAIGVYLEP    141
          +   +I GFF  G   +++AIG Y+
Set X2    SNSRIVGFFAHGEDYIEAIGAYVRT    822
```

Figure 14 Cont.

ref|XP_006663456.1| PREDICTED: disease resistance protein RPM1-like [Oryza brachyantha] (SEQ ID NO:8)
Sequence:
RPM1    RAGPWGGEGRRKHDIAVAPWRLESVRVSSGLVVDGIGFSYLDKSGKQHTTPLWGGAGGTV    1021
RPM1    RMVHLAPSEFVKEVSGTYGPSSFPSVITSLQLRTNIRSYGPFGEPKGTTFRTRVKQNGS    1081
RPM1    IVGFFGHSTVYIDAIGVYIHP    1102

*Sequence Alignment with Banlec (SEQ ID NO:9) highlighting the 2 hyrophobic residues in the loop:*
BanLec  KVGAWGGNGGSAFDMGPAY-RIISVKIFSGDVVDGVDVTFTY--YGKTETRHYGGSGGTP    62
        + G WGG G    D+   A  R+ SV++ SG VVDG+  ++      +  T  +GG+GGT
RPM1    RAGPWGGEGRRKHDIAVAPWRLESVRVSSGLVVDGIGFSYLDKSGKQHTTPLWGGAGGTV    1021

BanLec  HEIVLQEGEYLVGMAGEVANSSGAV-VLGKLGFSTNKKAYGPFGNTGGTPFSLPIA-AGK    120
        +  L   E++   ++G    +       V+  L   TN ++YGPFG   GT F  +    G
RPM1    RMVHLAPSEFVKEVSGTYGPSSFPSVITSLQLRTNIRSYGPFGEPKGTTFRTRVKQNGS    1081

BanLec  ISGFFGRGGKFLDAIGVYLEP    141
        I GFFG    ++DAIGVY+ P
RPM1    IVGFFGHSTVYIDAIGVYIHP    1102

SEQUENCE LISTING

<160> NUMBER OF SEQ ID NOS: 9

<210> SEQ ID NO 1
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: Xaa = any amino acid

<400> SEQUENCE: 1

Gly Xaa Xaa Xaa Asp
1               5

<210> SEQ ID NO 2
<211> LENGTH: 141
<212> TYPE: PRT
<213> ORGANISM: Musa acuminata

<400> SEQUENCE: 2

Met Asn Gly Ala Ile Lys Val Gly Ala Trp Gly Gly Asn Gly Gly Ser
1               5                   10                  15

Ala Phe Asp Met Gly Pro Ala His Arg Ile Ile Ser Val Lys Ile Tyr
            20                  25                  30

Ser Gly Asp Val Val Asp Gly Val Asp Val Thr Phe Thr Ser Tyr Glu
        35                  40                  45

Lys Thr Glu Thr Arg His Phe Gly Gly Ser Gly Gly Thr Pro His Glu
    50                  55                  60

Ile Val Leu Gln Glu Gly Glu Tyr Leu Val Gly Met Thr Gly Glu Phe
65                  70                  75                  80

Ala Asn Tyr His Gly Val Val Val Gly Lys Leu Gly Phe Asn Thr
                85                  90                  95

Asn Lys Lys Ser Tyr Gly Pro Phe Gly Asn Thr Gly Gly Thr Pro Phe
            100                 105                 110

Ser Leu Pro Ile Val Ala Gly Lys Ile Ser Gly Phe Phe Gly Arg Gly
        115                 120                 125

Gly Gln Phe Leu Asp Ala Ile Gly Val Tyr Leu Glu Pro
    130                 135                 140

<210> SEQ ID NO 3
<211> LENGTH: 130
<212> TYPE: PRT
<213> ORGANISM: Oryza sativa

<400> SEQUENCE: 3

Lys Val Gly Pro Trp Gly Gly Asn Gly Gly Thr Pro Gln Asp Ile Thr
1               5                   10                  15

Glu Thr Pro Lys Arg Leu Glu Ser Ile Thr Ile Arg Ser Gly Glu Val
            20                  25                  30

Val Asp Ser Ile Ser Phe Ser Tyr Phe Asp Gln Ala Gly Gln Lys Arg
        35                  40                  45

Val Ala Gly Pro Trp Gly Gly Pro Gly Gly Asn Leu Asn Thr Ile Glu
    50                  55                  60

Leu Ser Ser Ser Glu Phe Leu Lys Glu Val Ser Gly Thr Phe Gly Thr
65                  70                  75                  80

Tyr Tyr Gly Ser Asn Val Ile Thr Ser Ile Lys Phe Val Thr Asn Val
                85                  90                  95

Lys Thr Tyr Gly Pro Phe Gly Lys Gln Asn Gly Thr Pro Phe Val Gly
            100                 105                 110

Phe Phe Gly Arg Gly Gly Lys Tyr Leu Asp Ala Val Gly Val Tyr Val
        115                 120                 125

His Pro
    130

<210> SEQ ID NO 4
<211> LENGTH: 137
<212> TYPE: PRT
<213> ORGANISM: Cycas rumphii

<400> SEQUENCE: 4

Gly Val Gly Lys Glu Gly Pro Tyr Gly Gly Val Gly Gly Ala Pro Trp

```
  1               5                   10                  15
Asp Asp Gly Pro Gln Phe Gly Ile Ser Arg Ile Leu Ile His Ser Gly
                20                  25                  30

Asp Val Val Asp Ser Ile Gln Val Asp His Arg Pro Lys His Gly Gly
                35                  40                  45

Pro Gly Gly Thr Ala Thr Glu Ile Gln Phe Asp Pro Asp Glu Val Leu
                50                  55                  60

Lys Lys Ile Glu Gly Tyr Phe Gly Pro Tyr Tyr Gly Arg Pro Ser Ile
 65                 70                  75                  80

Ile Lys Ser Leu Thr Ile His Thr Asn Leu Thr Lys Tyr Gly Pro Phe
                85                  90                  95

Gly Thr Ala Gly Gly Thr Gln Gly Asp Val His Phe Ala Ser Thr Ser
                100                 105                 110

Leu Glu His Gly Lys Ile Val Gly Phe Gly Arg Ala Ala Glu Tyr
                115                 120                 125

Leu Asp Ala Ile Gly Val Tyr Ile Ala
                130                 135
```

<210> SEQ ID NO 5
<211> LENGTH: 137
<212> TYPE: PRT
<213> ORGANISM: Cycas revoluta

<400> SEQUENCE: 5

```
Gly Val Gly Lys Glu Gly Pro Tyr Gly Gly Val Gly Gly Ala Pro Trp
 1               5                   10                  15

Asp Asp Gly Pro Gln Phe Gly Ile Ser Arg Ile Leu Ile His Ser Gly
                20                  25                  30

Asp Val Val Asp Ser Ile Gln Val Asp His Arg Pro Lys His Gly Gly
                35                  40                  45

Pro Gly Gly Ala Ala Thr Glu Ile Gln Phe Asn Pro Asp Glu Val Leu
                50                  55                  60

Lys Lys Ile Glu Gly Tyr Phe Gly Pro Tyr Tyr Gly Arg Pro Ser Ile
 65                 70                  75                  80

Ile Lys Ser Leu Thr Phe His Thr Asn Leu Thr Lys Tyr Gly Pro Phe
                85                  90                  95

Gly Thr Ala Gly Gly Thr Gln Gly Asp Val His Phe Ala Ser Thr Ser
                100                 105                 110

Leu Glu His Gly Lys Ile Val Gly Phe Phe Gly Arg Ala Ala Gln Tyr
                115                 120                 125

Leu Asp Ala Ile Gly Val Tyr Ile Ala
                130                 135
```

<210> SEQ ID NO 6
<211> LENGTH: 145
<212> TYPE: PRT
<213> ORGANISM: Setaria Italica

<400> SEQUENCE: 6

```
Gly Val Ala Arg Ile Gly Pro Trp Gly Gly Asp Arg Gly Val Leu His
 1               5                   10                  15

Asp Ile Thr Val Thr Pro His His Leu Glu Arg Val Thr Ile Phe Ser
                20                  25                  30

Gly Thr Ile Ile Asp Ser Leu Glu Phe Leu Tyr Ser Asp His Asp Gly
                35                  40                  45

Lys Gln His Thr Ala Gly Pro Trp Gly Gly Cys Gly Gly Gly Gly Arg
```

```
            50                  55                  60
Lys Ile Arg Phe Asp Pro Ser Glu Phe Ile Val Lys Val Ser Gly Thr
 65                  70                  75                  80

Phe Cys Ala Trp His Gly Val Lys Asn Val Leu Ser Ser Leu Thr Leu
                 85                  90                  95

Val Thr Asn Thr Gly Arg Ser Tyr Gly Pro Tyr Gly Thr Glu Phe Gly
                100                 105                 110

Thr Ala Phe His Val Pro Glu Gln Ser Asn Ser Arg Ile Val Gly Phe
            115                 120                 125

Phe Ala His Gly Glu Asp Tyr Ile Glu Ala Ile Gly Ala Tyr Val Arg
        130                 135                 140

Thr
145

<210> SEQ ID NO 7
<211> LENGTH: 145
<212> TYPE: PRT
<213> ORGANISM: Setaria Italica

<400> SEQUENCE: 7

Gly Val Ala Arg Ile Gly Pro Trp Gly Gly Asp Arg Gly Val Leu His
  1               5                  10                  15

Asp Ile Thr Val Thr Pro His His Leu Glu Arg Val Thr Ile Phe Ser
                 20                  25                  30

Gly Thr Ile Ile Asp Ser Leu Glu Phe Leu Tyr Ser Asp His Asp Gly
                 35                  40                  45

Lys Gln His Thr Ala Gly Pro Trp Gly Gly Cys Gly Gly Gly Gly Arg
 50                  55                  60

Lys Ile Arg Phe Asp Pro Ser Glu Phe Ile Val Lys Val Ser Gly Thr
 65                  70                  75                  80

Phe Cys Ala Trp His Gly Val Lys Asn Val Leu Ser Ser Leu Thr Leu
                 85                  90                  95

Val Thr Asn Thr Gly Arg Ser Tyr Gly Pro Tyr Gly Thr Glu Phe Gly
                100                 105                 110

Thr Ala Phe His Val Pro Glu Gln Ser Asn Ser Arg Ile Val Gly Phe
            115                 120                 125

Phe Ala His Gly Glu Asp Tyr Ile Glu Ala Ile Gly Ala Tyr Val Arg
        130                 135                 140

Thr
145

<210> SEQ ID NO 8
<211> LENGTH: 141
<212> TYPE: PRT
<213> ORGANISM: Oryza brachyantha

<400> SEQUENCE: 8

Arg Ala Gly Pro Trp Gly Gly Glu Gly Arg Lys His Asp Ile Ala
  1               5                  10                  15

Val Ala Pro Trp Arg Leu Glu Ser Val Arg Val Ser Ser Gly Leu Val
                 20                  25                  30

Val Asp Gly Ile Gly Phe Ser Tyr Leu Asp Lys Ser Gly Lys Gln His
                 35                  40                  45

Thr Thr Pro Leu Trp Gly Gly Ala Gly Gly Thr Val Arg Met Val His
 50                  55                  60

Leu Ala Pro Ser Glu Phe Val Lys Glu Val Ser Gly Thr Tyr Gly Pro
```

```
                65                   70                   75                  80

Phe Phe Ser Phe Pro Ser Val Ile Thr Ser Leu Gln Leu Arg Thr Asn
                        85                   90                   95

Ile Arg Ser Tyr Gly Pro Phe Gly Glu Pro Lys Gly Thr Thr Phe Arg
                        100                  105                  110

Thr Arg Val Lys Gln Asn Gly Ser Ile Val Gly Phe Phe Gly His Ser
                        115                  120                  125

Thr Val Tyr Ile Asp Ala Ile Gly Val Tyr Ile His Pro
                        130                  135                  140

<210> SEQ ID NO 9
<211> LENGTH: 141
<212> TYPE: PRT
<213> ORGANISM: Musa acuminata

<400> SEQUENCE: 9

Met Asn Gly Ala Ile Lys Val Gly Ala Trp Gly Gly Asn Gly Gly Ser
1               5                   10                  15

Ala Phe Asp Met Gly Pro Ala Tyr Arg Ile Ile Ser Val Lys Ile Phe
                20                  25                  30

Ser Gly Asp Val Val Asp Gly Val Asp Val Thr Phe Thr Tyr Tyr Gly
            35                  40                  45

Lys Thr Glu Thr Arg His Tyr Gly Gly Ser Gly Gly Thr Pro His Glu
        50                  55                  60

Ile Val Leu Gln Glu Gly Glu Tyr Leu Val Gly Met Ala Gly Glu Val
65                  70                  75                  80

Ala Asn Tyr His Gly Ala Val Val Leu Gly Lys Leu Gly Phe Ser Thr
                85                  90                  95

Asn Lys Lys Ala Tyr Gly Pro Phe Gly Asn Thr Gly Gly Thr Pro Phe
                100                 105                 110

Ser Leu Pro Ile Ala Ala Gly Lys Ile Ser Gly Phe Phe Gly Arg Gly
            115                 120                 125

Gly Lys Phe Leu Asp Ala Ile Gly Val Tyr Leu Glu Pro
            130                 135                 140
```

LECTINS AND USES THEREOF

The present Application is a national phase application under 35 U.S.C. § 371 of PCT International Application No. PCT/US2015/050383, filed Sep. 16, 2015, which claims priority to U.S. Provisional Patent Application Ser. No. 62/051,081, filed Sep. 16, 2014, the disclosures of which are herein incorporated by reference in their entireties.

STATEMENT REGARDING FEDERALLY SPONSORED RESEARCH OR DEVELOPMENT

This invention was made with government support under NS062675 awarded by the National Institutes of Health. The Government has certain rights in the invention.

FIELD OF THE INVENTION

Provided herein are chemical compounds, methods for their discovery, and their therapeutic and research use. Further provided herein are antiviral and antimicrobial lectin compounds and methods of their use.

BACKGROUND

Acquired immune deficiency syndrome or acquired immunodeficiency syndrome (AIDS or Aids) is a collection of symptoms and infections resulting from the specific damage to the immune system caused by the human immunodeficiency virus (HIV) in humans (see, e.g., Marx, J. L. (1982) Science 217 (4560): 618-621; herein incorporated by reference in its entirety), and similar viruses in other species (SIV, FIV, etc.). The late stage of the condition leaves individuals prone to opportunistic infections and tumors. Although treatments for AIDS and HIV exist to slow the virus' progression, there is no known cure. HIV is transmitted through direct contact of a mucous membrane or the bloodstream with a bodily fluid containing HIV, such as blood, semen, vaginal fluid, preseminal fluid, and breast milk. This transmission can come in the form of anal, vaginal or oral sex, blood transfusion, contaminated hypodermic needles, exchange between mother and baby during pregnancy, childbirth, or breastfeeding, or other exposure to one of the above bodily fluids.

In the absence of antiretroviral therapy, the median time of progression from HIV infection to AIDS is nine to ten years, and the median survival time after developing AIDS is only 9.2 months (see, e.g., Morgan, et al., (2002) AIDS 16 (4): 597-632; herein incorporated by reference in its entirety). The use of highly active antiretroviral therapy prolongs both the median time of progression to AIDS and the median survival time.

There is currently no vaccine or cure for HIV or AIDS. The only known methods of prevention are based on avoiding exposure to the virus or, failing that, an antiretroviral treatment directly after a highly significant exposure, called post-exposure prophylaxis (PEP). PEP has a very demanding four week schedule of dosage. It also has very unpleasant side effects including diarrhea, malaise, nausea and fatigue. What is needed are improved methods for treating HIV and AIDS.

SUMMARY

Provided herein are chemical compounds, methods for their discovery, and their therapeutic and research use. Further provided herein are antiviral and antimicrobial lectin compounds and methods of their use.

For example, in some embodiments, provided herein is a composition comprising a variant lectin polypeptide comprising at least one mutation that disrupts pi-pi aromatic stacking, wherein the variant lectin polypeptide exhibits antiviral or antimicrobial activity, and wherein the polypeptide exhibits reduced mitogenic activity relative to a wild type polypeptide. In some embodiments, the variant lectin polypeptide is selected from, for example, *Malus domestica* agglutinin alpha chain-like; *Oryza sativa* Indica Group hypothetical protein OsI_37872; *Theobroma cacao* Mannose-binding lectin superfamily protein; *Cycas rumphii* jacalin-related lectin; *Cycas revoluta* lectin; *Setari* 4714 *italica* mannose/glucose-specific lectin-like isoform X1; *Setaria* 4714 *italica* mannose/glucose-specific lectin-like isoform X2; or *Oryza* from rice brachyantha disease resistance protein RPM1-like. In some embodiments, the lectin is a lectin with one of the following variants: a lectin comprising mutations at positions 84 or 85 of SEQ ID NO:2; positions 244 or 245 of SEQ ID NO:3; positions 225 or 226 of SEQ ID NO:4; positions 225 or 226 of SEQ ID NO:5; positions 782 or 783 of SEQ ID NO:6; positions 761 or 762 of SEQ ID NO:7; or positions 1042 or 1043 of SEQ ID NO:8. In some embodiments, the variant is a non-aromatic amino acid. In some embodiments, the above-described amino acids are mutated to T, G, K, L, D, E, or Q. In some embodiments, the amino acids are substituted with T or G. In some embodiments, the composition is an anti-viral, anti-microbial, anti-fungal, and/or anti-parasitic pharmaceutical composition. In some embodiments, the composition treats or prevents infection by microorganisms presenting surface mannose. In some embodiments, the composition treats or prevents infection by a virus selected from, for example, HIV, corona virus or influenza virus.

Some embodiments provide a pharmaceutical composition comprising any of the aforementioned polypeptides and a pharmaceutically acceptable carrier.

Further embodiments provide methods and uses of treating and/or preventing infection by a microorganism comprising administering any of the aforementioned compositions. In some embodiments, the composition is administered topically. In some embodiments, the composition treats and/or prevents said infection systemically. In some embodiments, the infection is by a microorganism comprising surface mannose. In some embodiments, the microorganism is a virus, bacteria, parasite, or fungus. For example, in some embodiments, the virus is HIV, influenza, or corona virus. In some embodiments, the composition is administered to a subject diagnosed with an infection, at risk of an infection, or suspected of having an infection.

Additional embodiments provide medical devices or products (e.g., condoms) comprising any of the aforementioned compositions.

Additional embodiments are described herein.

DESCRIPTION OF THE FIGURES

FIG. 14 shows an alignment of BanLec and additional lectins from other species. Amino acids that participate in pi-pi stacking are highlighted.

DEFINITIONS

Figure 1:
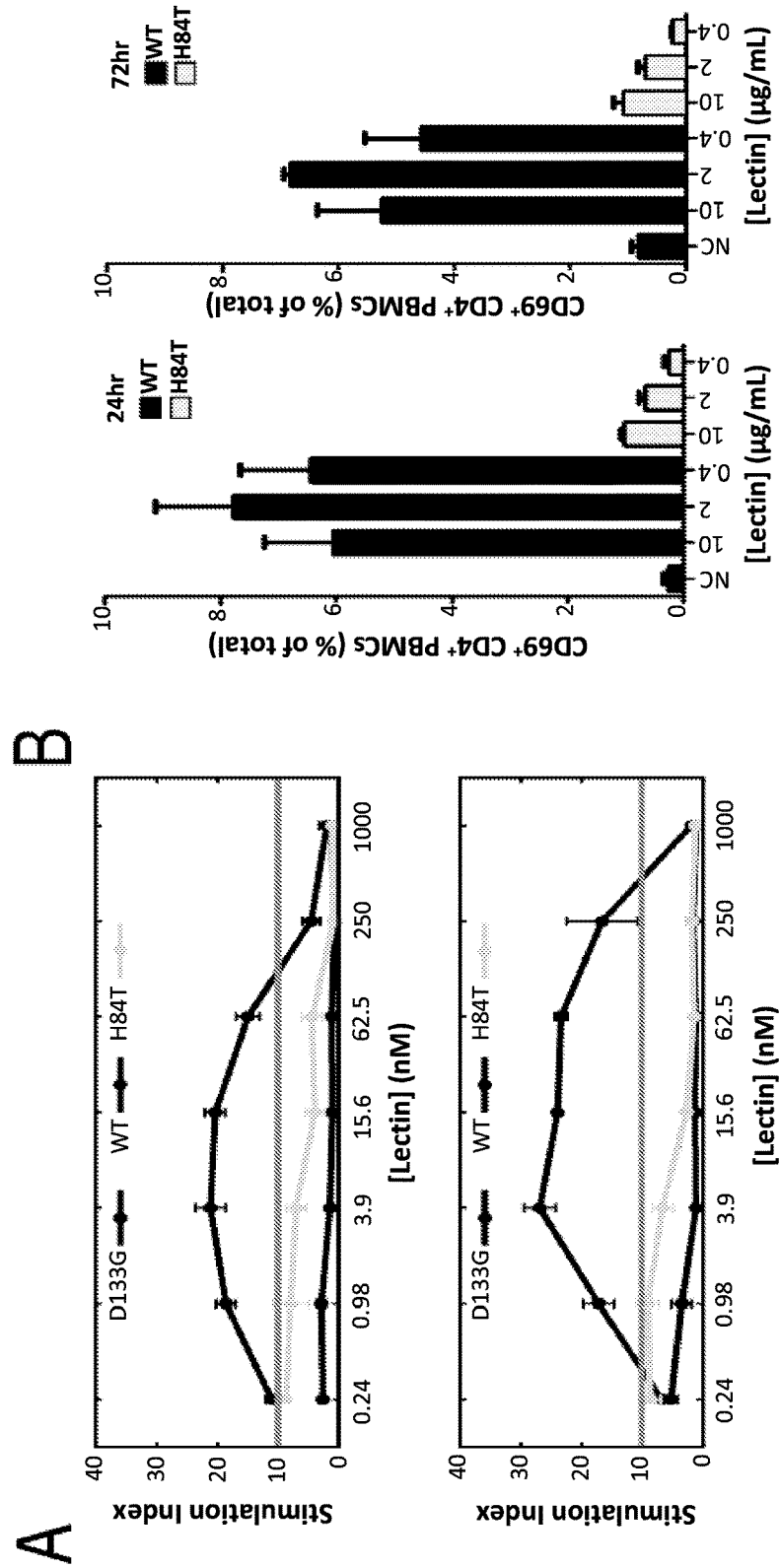
FIG. 1 shows that H84T BanLec mutant is significantly less mitogenic than is WT BanLec. (A) Comparisons of the mitogenic activity of H84T to recombinant WT BanLec. (B) Induction of the activation marker CD69 on CD4 T cells in the presence of WT BanLec or the H84T mutant as measured by flow cytometry, one day or three days post-treatment. (C) Induction of cytokines/chemokines by WT BanLec and the H84T mutant. PBMCs from healthy donors were incubated for 72 hrs with BanLec at 2 µg/ml, respectively.
Figure 1:
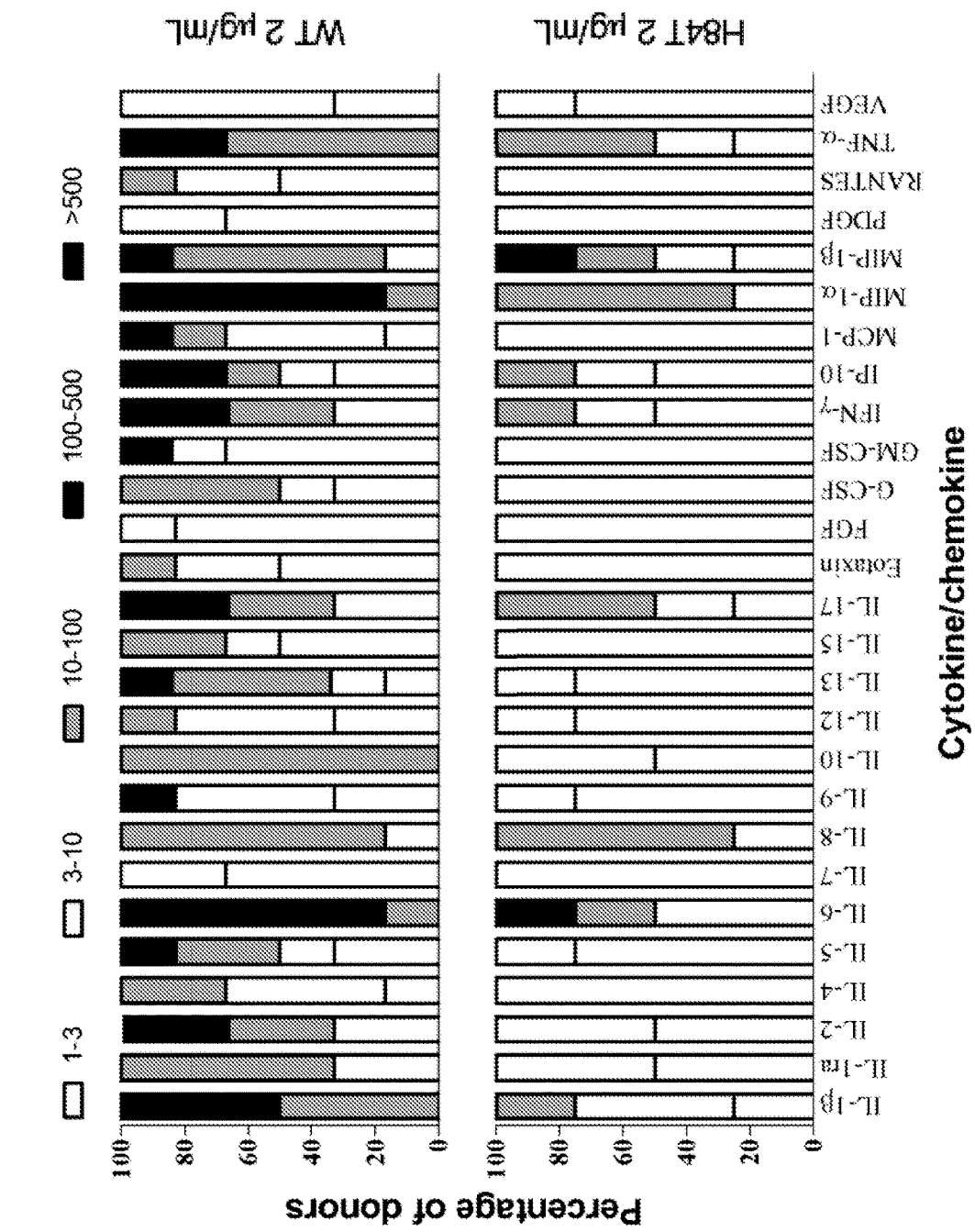

To facilitate an understanding of the present disclosure, a number of terms and phrases are defined below.

As used herein, the term "subject" refers to organisms to be treated by the methods of embodiments of the present disclosure. Such organisms preferably include, but are not limited to, mammals (e.g., murines, simians, equines, bovines, porcines, canines, felines, and the like), and most preferably includes humans. In the context of the disclosure, the term "subject" generally refers to an individual who will receive or who has received treatment (e.g., administration of a peptide of the present disclosure and optionally one or more other agents) for a condition characterized by infection by a microorganism or risk of infection by a microorganism.

The term "diagnosed," as used herein, refers to the recognition of a disease by its signs and symptoms (e.g., resistance to conventional therapies), or genetic analysis, pathological analysis, histological analysis, diagnostic assay (e.g., for microorganism infection) and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "effective amount" refers to the amount of a therapeutic agent (e.g., a peptide of the present disclosure) sufficient to effect beneficial or desired results. An effective amount can be administered in one or more administrations, applications or dosages and is not intended to be limited to a particular formulation or administration route.

As used herein, the term "co-administration" refers to the administration of at least two agent(s) (e.g., a peptide of the present disclosure) or therapies to a subject. In some embodiments, the co-administration of two or more agents/therapies is concurrent. In some embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

The term "sample" as used herein is used in its broadest sense. A sample may comprise a cell, tissue, or fluids, nucleic acids or polypeptides isolated from a cell (e.g., a microorganism), and the like.

As used herein, the terms "purified" or "to purify" refer, to the removal of undesired components from a sample. As used herein, the term "substantially purified" refers to molecules that are at least 60% free, preferably 75% free, and most preferably 90%, or more, free from other components with which they usually associated.

As used herein, the term "modulate" refers to the activity of a compound (e.g., a compound of the present disclosure) to affect (e.g., to kill or prevent the growth of) a microorganism.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., infection by a microorganism). Test compounds comprise both known and potential therapeutic compounds. A test compound can be determined to be therapeutic by using the screening methods of the present disclosure. A "known therapeutic compound" refers to a therapeutic compound that has been shown (e.g., through animal trials or prior experience with administration to humans) to be effective in such treatment or prevention. In some embodiments, "test compounds" are agents that treat or prevent infection by a microorganism.

The term "label" as used herein refers to any atom or molecule that can be used to provide a detectable (preferably quantifiable) effect, and that can be attached to a nucleic acid or protein. Labels include but are not limited to dyes; radiolabels such as $^{32}P$; binding moieties such as biotin; haptens such as digoxgenin; luminogenic, phosphorescent or fluorogenic moieties; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable.

DETAILED DESCRIPTION

Provided herein are chemical compounds, methods for their discovery, and their therapeutic and research use. Further provided herein are antiviral and antimicrobial lectin compounds and methods of their use.

Experiments described herein utilized BanLec and demonstrated that replacing the histidine at position 84 with a threonine, significantly reduces its mitogenic activity while preserving its antiviral potency in vivo. The mutant protein agglutinates erythrocytes much less actively and is more susceptible to glycocluster inhibition when interacting with polyvalent surfaces. X-ray crystallography, NMR spectroscopy, and bioassays on this and a panel of other BanLec mutants reveal that the loss of mitogenicity is correlated with a conformational change involving the loss of pi-pi stacking between the aromatic amino acids H84 and Y83 and an increase in conformational flexibility. These alterations affect contact formation with di- and pentamannosides and the topological presentation of the sugar binding region. Thus, by fine-tuning sugar binding sites, target selection and downstream effects of a lectin can be modulated so as to knock down one functional activity while preserving another.

Accordingly, in some embodiments, the present disclosure provides lectins where the mitogenicity has been separated from the anti-microbial properties. In some embodiments, the present disclosure provides lectins from other species that have mutations that involve the loss of pi-pi stacking and thus have decreased mitogenicity. For example, FIG. 14 shows an alignment of BanLec and additional lectins from other species Amino acids that participate in pi-pi stacking are highlighted. In some embodiments, lectins that have two sugar-binding sites separated by a loop, with the latter containing two aromatic amino acids next to each other that can engage in pi-pi stacking are utilized. Examples include, but are not limited to, *Malus domestica* agglutinin alpha chain-like (ref|XP_008348486.1); *Oryza sativa* Indica Group hypothetical protein OsI_37872 (gb|EAY82651.1); *Theobroma cacao* Mannose-binding lectin superfamily protein (ref|XP_007024409.1); *Cycas rumphii* jacalin-related lectin (dbj|BAG24500.1); *Cycas revoluta* lectin (dbj|BAE95375.1); *Setari* 4714 *italica* mannose/glucose-specific lectin-like isoform X1 (ref|XP_004979669.1); *Setaria* 4714 *italica* mannose/glucose-specific lectin-like isoform X2 (ref|XP_004979670.1); and *Oryza* from rice brachyantha disease resistance protein RPM1-like (ref|XP_006663456.1).

In some embodiments, the residues that engage in pi-pi stacking are mutated to amino acids that are unable to engage in pi-pi stacking. In some embodiments, aromatic amino acids (e.g., phenylalanine, tryptophan, histidine, or tyrosine) are modified to prevent pi-pi stacking. Any mutation that results in a reduction or decrease in mitogenicity while retaining anti-viral properties is contemplated to be within the scope of the present disclosure. In some embodiments, the lectin comprises mutations at positions 84 or 85 of SEQ ID NO:2; positions 244 or 245 of SEQ ID NO:3; positions 225 or 226 of SEQ ID NO:4; positions 225 or 226 of SEQ ID NO:5; positions 782 or 783 of SEQ ID NO:6; positions 761 or 762 of SEQ ID NO:7; or positions 1042 or 1043 of SEQ ID NO:8. In some embodiments, the above-described amino acids are mutated to non-aromatic amino acids. In some embodiments, the above-described amino acids are mutated to T, G, K, L, D, E, or Q. In some embodiments, the amino acids are substituted with T or G.

In some embodiments, the present disclosure provide variant lectin polypeptides that exhibit reduced mitogentic activity relative to the wild type lectin (e.g., the mitogenic activity is reduced at least 10%, at least 20%, at least 50%, at least 75%, at least 85%, at least 90%, at least 95% etc) relative to wild type lectins.

In some embodiments, conservative or non-conservative substitutions (e.g., at the positions described above or other positions) are made. For example, it is contemplated that isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, histidine, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic hydroxyl; (4) aromatic (phenylalanine, tyrosine, tryptophan); (5) amide (asparagine, glutamine); and (6) sulfur containing (cysteine and methionine) (e.g., Stryer ed., Biochemistry, pg. 17-21, 2nd ed, WH Freeman and Co., 1981).

"Nonconservative" changes (e.g., replacement of a glycine with a tryptophan) are also contemplated. Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

In some embodiments, the polypeptide may be a naturally purified product, a product of chemical synthetic procedures, or produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide is glycosylated or non glycosylated.

In some embodiments, polynucleotides encoding variant lectin polypeptides are produced by recombinant techniques. Thus, for example, the polynucleotide may be included in any one of a variety of expression vectors for expressing a polypeptide. In some embodiments, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

Large numbers of suitable vectors are available, and are commercially available. Such vectors include, but are not limited to, the following vectors: 1) Bacterial—pQE70, pQE60, pQE 9 (Qiagen), pBS, pD10, phagescript, psiX174, pbluescript SK, pBSKS, pNH8A, pNH16a, pNH18A, pNH46A (Stratagene); ptrc99a, pKK223 3, pKK233 3, pDR540, pRIT5 (Pharmacia); and 2) Eukaryotic—pWL-NEO, pSV2CAT, pOG44, PXT1, pSG (Stratagene) pSVK3, pBPV, pMSG, pSVL (Pharmacia). Any other plasmid or vector may be used as long as they are replicable and viable in the host. In some embodiments, mammalian expression vectors comprise an origin of replication, a suitable promoter and enhancer, and also any necessary ribosome binding sites, polyadenylation sites, splice donor and acceptor sites, transcriptional termination sequences, and 5' flanking non transcribed sequences. In other embodiments, DNA sequences derived from the SV40 splice, and polyadenylation sites may be used to provide the required non transcribed genetic elements.

In certain embodiments, the DNA sequence in the expression vector is operatively linked to an appropriate expression control sequence(s) (promoter) to direct mRNA synthesis. Exemplary promoters include, but are not limited to, the LTR or SV40 promoter, the *E. coli* lac or trp, the phage lambda PL and PR, T3 and T7 promoters, and the cytomegalovirus (CMV) immediate early, herpes simplex virus (HSV) thymidine kinase, and mouse metallothionein I promoters and other promoters known to control expression of gene in prokaryotic or eukaryotic cells or their viruses. In some embodiments, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments, transcription in higher eukaryotes is increased by inserting an enhancer sequence into the vector. Enhancers are cis acting elements of DNA, usually about from 10 to 300 bp that act on a promoter to increase its transcription. Enhancers include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In some embodiments, the vector includes appropriate sequences for amplifying expression.

In some embodiments, lectin polypeptides are produced in host cells. In some embodiments, the host cell is a higher eukaryotic cell (e.g., a mammalian or insect cell). In other embodiments, the host cell is a lower eukaryotic cell (e.g., a yeast cell). In some embodiments, the host cell is a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS 7 lines of monkey kidney fibroblasts, (Gluzman, Cell 23:175 [1981]), C127, 3T3, 293, 293T, HeLa and BHK cell lines.

Proteins can be expressed in mammalian cells, yeast, bacteria, or other cells under the control of appropriate promoters. Cell free translation systems can also be employed to produce such proteins using RNAs derived from the DNA constructs. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

In some embodiments, peptides comprise labels or purification tags (e.g., to aid in purification of lectin polypeptides). For example, in some embodiments, nucleic acids encoding lectin polypeptides are fused in frame to a marker sequence which allows for purification of the polypeptide. A non-limiting example of a marker sequence is a hexahistidine tag which may be supplied by a vector, preferably a pQE 9 vector, which provides for purification of the polypeptide fused to the marker in the case of a bacterial host, or, for example, the marker sequence may be a hemagglutinin (HA) tag when a mammalian host (e.g., COS 7 cells) is used. The HA tag corresponds to an epitope derived from the influenza hemagglutinin protein (Wilson et al., Cell, 37:767 [1984]).

The mutant lectins described herein find use in a variety of applications. For example, in some embodiments, non-mitogenic lectins (e.g., variants of SEQ ID NOs: 2-7) find use in therapeutic compositions to treat viral infections (e.g., HIV, influenza, SARS, or other respiratory viruses). In some embodiments, non-mitogenic lectin polypeptides are used in combinations with known therapeutic agents (e.g., as part of a therapeutic cocktail).

In some embodiments, lectin compositions (e.g., variants of SEQ ID NOs:2-8 as described herein) are used as a component of topical antiviral compositions (e.g., to kill HIV and thus prevent infection). For example, in some embodiments, lectins are included in formulations for use as vaginal anti-viral agents (e.g., to be used prior to or following contact with bodily fluids (e.g., sperm) containing or suspected of containing HIV). In some embodiments, antiviral formulations comprising lectins are used to treat medical devices, barrier devices (e.g., condoms), or other objects likely to contact bodily fluids containing HIV or other pathogenic viruses.

The lectins described herein find use in the prevention or treatment of other viral infections of humans, animals, and plants. In some embodiments, compositions described herein are not limited to antiviral applications. In some embodiments, compositions find use as anti-microbial, anti-bacterial, anti-parasitic, and anti-fungal agents. For example, in some embodiments, the present disclosure provides compositions and methods to treat or prevent infections of viruses including but not limited to: HIV, HCV, Dengue virus, Marburg virus, Ebola virus, influenza, West Nile virus, Cytomegalovirus, Herpes virus (e.g., type 8), Corona virus (e.g, SARS), and Measles virus. In some embodiments, the present disclosure provides compositions and methods to treat or prevent infections of bacteria including but not limited to: *Mycobacterium tuberculosis, Mycobacterium leprae, Mycobacteriumbovis, Streptococcus pneumoniae* (e.g., serotypes 3 and 14), *Helobacter pilori*, and *Lactobacillus* spp. In some embodiments, the present disclosure provides compositions and methods to treat or prevent infections of parasites including but not limited to: *Leshmania infantum, Leshmania pifanoi, Leshmania mexicana*, and *Schistosoma mansoni* parasite. In some embodiments, the present disclosure provides compositions and methods to treat or prevent infections of fungi including but not limited to: *Aspergillus fumigatus* and *Candida albicans*.

In some embodiments, compositions find use in treating infections involving organisms presenting appropriate surface sugars (e.g., mannose). In some embodiments, use of the compositions is not limited to surface application. In some embodiments, compositions are administrated by any suitable delivery route understood by those in the pharmaceutical field (e.g., intravenous, oral, topical, etc.).

Embodiments of the present disclosure further provide pharmaceutical compositions (e.g., comprising one or more of the therapeutic agents described above). The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration (e.g., to tissues, wounds, organs, etc) may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present disclosure may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active agents of the formulation.

Dosing is dependent on severity and responsiveness of the disease state or condition to be treated, with the course of treatment lasting from several days to several months, or until a cure is effected or a diminution of the disease state is achieved. In some embodiments, treatment is administered in one or more courses, where each course comprises one or more doses per day for several days (e.g., 1, 2, 3, 4, 5, 6) or weeks (e.g., 1, 2, or 3 weeks, etc.). In some embodiments, courses of treatment are administered sequentially (e.g., without a break between courses), while in other embodiments, a break of 1 or more days, weeks, or months is provided between courses. In some embodiments, treatment is provided on an ongoing or maintenance basis (e.g., multiple courses provided with or without breaks for an indefinite time period). Optimal dosing schedules can be calculated from measurements of drug accumulation in the body of the patient. The administering physician can readily determine optimum dosages, dosing methodologies and repetition rates.

In some embodiments, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues.

EXPERIMENTAL

The following examples are provided in order to demonstrate and further illustrate certain preferred embodiments and aspects of the present disclosure and are not to be construed as limiting the scope thereof.

Example 1

Methods
Lectins and Carbohydrates

Methyl α-d-mannopyranoside and PHA-L were obtained from Sigma. The lectin Griffithsin was obtained from the NIH AIDS Reagent and Reference Program. The lectins GNA and BanLec were isolated through previously described methods (Vandamme et al., Febs Lett 215, 140-144 1987). Isolation of recombinant BanLec from *E. coli* is described below.

Construction and Mutation of BanLec Expression Vectors

A cDNA encoding a codon-optimized BanLec for expression in *E. coli* was generated from the protein sequence gi71042661 by Genscript. The cDNA was then cloned into the *E. coli* expression vector pET240b (Novagen) to be in frame with the 6xHis tag. Site-directed mutations were introduced by the QuikChange Multi Site-Directed Mutagenesis Kit or by the QuikChange Lightning Multi Site-Directed Mutagenesis Kit (Stratagene). PCR primers for introduction of the desired mutations were designed using the QuikChange Primer Design Program; available from Stratagene.

Purification of Recombinant BanLec and Mutants

A plasmid containing either the WT or a mutant form of BanLec was used to transform MDS 42 T7 or RosettaBlue pLysS *E. coli* cells. An overnight culture was used to inoculate 2xYT media. When the $OD_{600}$ of the culture reached 0.7-1.0, protein expression was induced with IPTG at a final concentration of 1 mM. Five hours post induction, the bacteria were harvested and the cell pellets were frozen and stored at −20° C. until further processing. Recombinant protein was isolated by resuspending the pellet in 5 ml of 50 mM Tris, 0.5 M NaCl, and 0.02% $NaN_3$ at pH 8.0 (the buffers will be referred to hereafter as IMAC-#, where # represents the amount of imidazole in mM) per 100 mL of culture grown. Lysozyme and DNAse I were added to reach concentrations of 1 mg/mL and 5 µg/mL, respectively. The mixture was incubated at room temperature for 30 minutes with constant stirring. After the incubation, an equal volume of IMAC-50 buffer was added and the mixture was chilled on ice. Cells were further lysed with four rounds of 30 seconds of pulsed sonication at the 50% duty at power level 5 while on ice, followed by a one minute rest period between each 30 seconds of sonication. The insoluble material was pelleted by centrifugation at 10,000xg for 20 minutes.

The resulting cleared lysate was added to Ni-NTA agarose (Qiagen) that had been equilibrated with IMAC-25 buffer. The lysate and the resin were incubated for one hour at 4° C. with orbital rotation. The column was returned to room temperature and the lysate was allowed to pass through the column via gravity. The column was then washed with IMAC-25 buffer until the flow-through had an absorbance value at $280_{nm}$ less than 0.05. Elution of the protein was then performed with IMAC-250 buffer. The protein was then dialyzed against PBS using Slide-alyzer dialysis cassettes with a 10 kDa molecular weight cut-off (Pierce). Two 2-hour dialysis procedures were performed at 4° C. against a volume greater than 200 times that of protein sample followed by overnight dialysis. The protein was then sterile-filtered through a 0.22 µm filter. The protein was aliquoted and stored at −80° C. prior to use, where it could then be stored again at 4° C. for short-term use. Protein content of solutions was quantified by BCA (Pierce) using bovine serum albumin protein as a standard.

Production of Pseudotyped HIV

Virus was produced using previously described methods (Yang et al., Hum Gene Ther 10, 123-132 1999). Briefly, production of pseudo-typed virus was performed by co-transfecting 293FT cells with a plasmid containing a proviral genome with a deletion in the envelope gene along with a plasmid that expresses an HIV-1 envelope gene. The following morning, the medium was changed. Forty-eight hours post transfection, the supernatant was collected and centrifuged at approximately 300xg for five minutes to remove any contaminating cells. For NL4-3 virus production, 293FT cells were transfected with the pNL4-3 plasmid. Virus was harvested as described above. Virus was quantified by determining titers with TZM-bl cells or by measuring p24 antigen by ELISA.

Assessment of Anti-HIV Activity

To each well of a white 96-well plate, 100 µL of TZM-BL cells resuspended at $1 \times 10^5$ cells/mL in DMEM medium with 25 mM HEPES and 10% FBS were added. The next day, the medium was removed by aspiration and fresh medium containing lectin or PBS as a control was added to the plate at a concentration 2-fold higher than the final concentration. After 30 minutes of incubation, virus diluted with medium was added and the cells were incubated for 48 hours at 37° C. After the incubation, 100 µL of medium were removed and replaced with 100 μL of ONE-Glo™ Luciferase reagent (Promega) for determination of luciferase expression.

Haemagglutination Assay

The haemagglutinating activity of the lectin was determined by a 2-fold serial dilution procedure using formaldehyde-treated rabbit erythrocytes. The haemagglutination titer was defined as the reciprocal of the highest dilution still exhibiting haemagglutination.

Isothermal Titration Calorimetry

Binding constants of the lectins for methyl-α-D-mannopyranoside were determined by isothermal titration calorimetry using a MicroCal VP-ITC calorimeter (Micro-Cal, Northampton, Mass., USA) at 25° C. Data were analyzed using Origins Ver. 7 software supplied with the instrument. The lectin in PBS, generally at approx. 0.2 mM, was titrated with the ligand at 20 mM in the same buffer. The titration volumes were adjusted so that the titration proceeded to at least a 10-fold molar excess of ligand over lectin monomers. The relatively low binding constants ($K_a$<1000 $M^{-1}$) precluded obtaining full saturation or a definite sigmoidal titration curve from which a definitive stoichiometry can be calculated; thus, the stoichiometry was fixed at 1 for curve-fitting to determine $K_a$; values between about 0.5 and 2-3 had little effect on the $K_a$-value obtained.

Assessment of Mitogenic Activity by BrdU Incorporation

PBLs were isolated as previously described, and resuspended in IMDM medium containing 10% FBS (IMDM-10) at a concentration of $2 \times 10^6$ cells/mL (Swanson et al., J Biol Chem 285, 8646-8655 2010). 50 μL of cell suspension were added per well of a white 96-well plate followed by 50 μL of IMDM-10 medium containing lectin at various concentrations or PBS. The cells were incubated at 37° C. for three days prior to an 18 hour addition of BrdU. Proliferation was measured by BrdU incorporation, which was detected via a chemiluminescent-ELISA (Cell Proliferation ELISA (chemiluminescent), Roche) as per the manufacturer's instructions. Mitogenic activity was quantified as a stimulation index, which is the signal of the stimulated cells divided by the signal of the untreated control cells (RLU of treated PBL/RLU of untreated PBL).

Flow Cytometry to Measure Cellular Activation

The expression of cellular activation markers was measured after a 3-day incubation of PBMCs with varying concentrations of MVN or CV-N at 37° C. Briefly, after washing with PBS containing 2% FBS, cells were incubated with solution containing FITC-labeled anti-CD4 mAb in combination with PE-labeled anti-CD25, anti-CD69, or anti-HLA-DR mAbs for 30 min at 4° C. For assessing non-specific (antigen-independent) background staining, cells were stained in parallel with Simultest Control IgG γ1/γ2a (BD Biosciences). Finally, the cells were washed, fixed with 1% formaldehyde solution, and analyzed with a FACSCalibur, resulting data were processed with CellQuest software and analyzed with the FLOWJO software.

Bio-Plex Cytokine Assay

PBMCs were cultured in the presence of several concentrations of lectin and culture supernatant was collected after 72 h. The cytokine production profile was determined by the Bio-Plex 200 system (Bio-Rad, Hercules, Calif.) and Bio-Plex Human Cytokine 27-plex assay according to the manufacturer's instructions. The 27-plex assay kit contains beads conjugated with mAbs specific for interleukin-1α (IL-1α), IL-1ra, IL-2, IL-4, IL-5, IL-6, IL-7, IL-8, IL-9, IL-10, IL-12, IL-13, IL-15, IL-17, eotaxin, fibroblast growth factor (FGF), granulocyte colony-stimulating factor (G-CSF), granulocyte-macrophage CSF (GM-CSF), interferon-γ (IFN-γ), interferon-inducible protein-10 (IP-10), monocyte chemoattractant protein-1 (MCP-1), macrophage inflammatory protein-1α (MIP-α), MIP-1β, platelet-derived growth factor-BB (PDGF-BB), regulated on activation normal T-cell expressed and secreted (RANTES), tumor necrosis factor-α (TNF-α), and vascular endothelial growth factor (VEGF). For each cytokine, nine standards ranging from 0.5 to 32,000 pg/mL were run in parallel and the minimum detectable dose was between 0.5-5 pg/mL. Standard curves and the concentrations of the cytokines within the samples were calculated with the Bio-Plex Manager 4.1 software.

Assessment of Anti-Influenza Activity

Pseudotyped lentiviral vectors that transduce a luciferase reporter gene were produced as previously described by calcium phosphate mediated transfection (Yang et al., Science 317, 825-828 2007). Haemagglutinin and neuraminidase expression plasmids (Wei et al., Science 329, 1060-1064 2010; Yang et al., 2007, supra) were obtained from Gary Nabel (Vaccine Research Center, NIH). H1N1 pseudotypes were produced using pVRC-7730 (A/South Carolina/1/18(H1N1)HA-wt) and pVRC-9259 (A/Brevig Mission/1/18(H1N1) NA). H5N1 viruses were produced using pVRC 7705 (A/Thailand/1(KAN-1)/2004/(H5N1) HA-wt) and pVRC-7708 (A/Thailand/1(KAN-1)/2004 NA/h). 293T cells in a 10 cm dish were co-transfected with 800 ng of HA plasmid, 100 ng of NA expression vector, 6.9 μg of pCMV Sport/h TMPRSS2 (a human type II transmembrane serine protease TMPRSS2 expression vector for the proteolytic activation of HA), 12 μg of pCMVΔR8.2, and 7.1 μg of pHR'CMV-Luc. Forty-eight hours post-transfection, supernatants were harvested, filtered (0.45 μm), and used to infect fresh 293T cells.

The day before infection, $1.25 \times 10^4$ 293 T cells in 100 μL DMEM medium containing 10% fetal bovine serum and 50 μg/mL geneticin were added to each well in 96-well tissue culture plates. Dilutions of BanLec were mixed with pseudotyped HIV-1 immediately before adding to cells. After two days, the culture medium was removed and the cells lyzed using Steady-Glo® Luciferase reagent (Promega). Cell lysates were transferred to a white opaque 96-well plate and the extent of luminescence was measured using a luminometer (Tecan). The amount of pseudotyped virus used in this experiment was selected by titration on 293T cells to assure that the luciferase activity was in the linear response range of the assay system. The data are shown relative to the amount of luciferase activity produced in cells infected with pseudotyped lentiviral vectors pre-treated with control buffer (PBS). Error bars represent standard error from duplicate determinations.

Vaginal HIV-1 Transmission

BLT mice (Wahl et al., PLoS pathogens 8, e1002732 2012) were anesthetized and received 75 μg of H84T BanLec (resuspended in PBS) vaginally in a volume of 20 μL. Ten minutes after application of the lectin, the mice were challenged vaginally by 175,000 TCIU of HIV-1 JR-CSF. Mice were bled weekly and the plasma was analyzed for the presence of viral RNA for six weeks as described previously (Denton et al., J Virol 86, 630-634 2012).

Glycocluster Assays

Neoglycoprotein (bovine serum albumin as carrier presenting 24-28 derivatives of mannose after covalent conjugation by applying an activation of p-aminophenyl derivatives with thiophosgene (McBroom et al., Methods Enzymol 28, 212-219 1972) and checked for lectin reactivity (Gabius et al., Cancer 61, 1125-1131 1988) was adsorbed to the plastic surface of microtiter plate wells (0.5 μg) establishing the matrix for binding the biotinylated lectins, which was quantitatively assessed spectrophotometrically by applying the streptavidin/β-galactosidase conjugate and the chromogen chlorophenolred-β-d-galactopyranoside as described (André et al., Glycobiology 9, 1253-1261 1999). Titrations of the extent of binding with increasing amounts of inhibitor were performed to determine the concentration that reduces the signal intensity of positive controls to 50% ($IC_{50}$-value). The glycoclusters (bivalent phenylenediamine-based glycocylophane (1) and terephthalamide-based compounds 2, 3, mannose-presenting tetra- to dodecavalent glycoclusters (4-8), and maltose-containing bi- to tetravalent glycoclusters based on propargyl-derivatized alcohols 9-111; See FIG. 3) (André et al., Mol Pharm 7, 2270-2279 2010; André et al., Org Biomol Chem 1, 3909-3916 2003; André et al., Org Biomol Chem 7, 4715-4725 2009b; Papadopoulos et al., Mol Pharmaceut 9, 394-403 2012) were individually tested (further details are described in the legend for Table 2 below). Cell assays were performed with the human SW480 colon adenocarcinoma line processed in FACScan runs using the fluorescent streptavidin/R-phycoerythrin complex (Sigma; 1:40) as indicator (Kopitz et al., Mol Pharmaceut 10, 2054-2061 2013). A non-cognate sugar (galactose) was used in parallel as an osmolarity control. Treatment of cells for 24 h with 150 µM 1-deoxymannojirimycin was performed to increase presentation of high-mannose-type N-glycans. Routinely, aliquots of a cell suspension were analyzed in parallel in triplicate with positive and negative controls and up to five independent series, with standard deviations not exceeding 13.9% after normalization of the data.

Crystallization, Data Collection and Structure Determination

Recombinant BanLec (WT and H84T mutant) was concentrated to approximately 5 mg/mL in buffer (10 mM HEPES, pH 7.5) containing 150 mM NaCl. Crystals appeared overnight in drops containing equal volumes of protein and well solution (10-20% PEG 8000 and 50-200 mM potassium phosphate). For the structures of BanLec in complex with dimannose (Sigma), crystals were soaked in 50 mM dimannose in well solution for 2.5 hours. All crystals were cryoprotected in well solution containing 20% glycerol prior to flash freezing in liquid nitrogen.

All data were collected at LS-CAT at the Advanced Photon Source at Argonne National Lab. Data for WT, WT+dimannose and H84T+dimannose were collected on line 21-ID-D, while data for H84T were collected on line 21-ID-G. Both lines were equipped with Mar300 detectors. Data were processed and scaled with HKL2000 (Otwinowski and Minor, Method Enzymol 276, 307-326 1997). The structures were solved by molecular replacement with Phaser (CCP4 suite) (Mccoy et al., J Appl Crystallogr 40, 658-674 2007) using the previously solved structure of banana lectin (2BMY) as a starting model. The structures of WT, WT+dimannose and H84T+dimannose BanLec were refined using Buster (Bricogne G., 2011) with iterative rounds of fitting in COOT (Emsley et al., Acta Crystal D 66, 486-501 2010). The structure of H84T was refined using REFMAC (Winn et al., Methods in enzymology 374, 300-321. 2003). Structures were validated with Molprobity (Chen et al., Acta Crystal D 66, 12-21 2010), Parvati (Zucker et al., Acta Crystal D 66, 889-900 2010), and whatcheck (Hooft et al., Nature 381, 272 1996). Ligand statistics were obtained from the Uppsala Electron-Density Server (Kleywegt et al., Acta Crystal D 60, 2240-2249 2004). Data refinement and statistics are given in Tables 3 and 4.

NMR Spectroscopy

Figure 7:
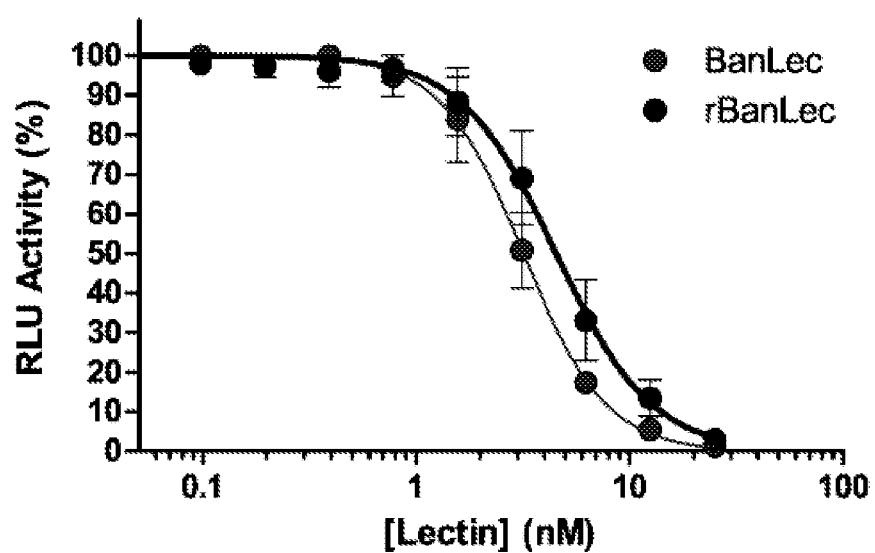
FIG. 7 shows a comparison of the anti-HIV-1 activities of natural and recombinant BanLec.

NMR spectra used for the assignment of BL-Y46K/V66D in solubility buffer (25 mM acetate, 50 mM KCl, 50 mM arginine, 50 mM glutamic acid, 1 mM EDTA, 2.5 mM $NaN_3$, 1.5% Triton-X-100, 10% $D_2O$, pH 5.3) were acquired at 313K on a 600 MHz Varian spectrometer equipped with a triple resonance cryo-probe with pulse field gradient. HN, N, CO, CA and CB assignments were obtained using a TROSY version of the following set of tridimensional experiments: HNCO, HNCA, HN(CA)CO, HN(CO)CA, CBCA(CO)NH, HNCACB (Sattler et al., Prog NMR Spectrosc 34, 93-158 1999). All spectra were processed using NMRPipe (Delaglio et al., J Biomol NMR 6, 277-293 1995) and analyzed using Sparky (Goddard, Sparky 3. (University of California, San Francisco, USA) 2008). The assignment of the spin system was realized using the program MARS (Jung and Zweckstetter, J Biomol NMR 30, 11-23 2004). Assignments were transferred onto the NH-HSQC spectra of WT BanLec by overlay in Sparky. Assignments were further verified by comparison of a panel of NH-HSQC spectra of BanLec mutants in which chemical shifts occurred in correspondence with the assigned mutation Results The Antiviral and Mitogenic Activity of BanLec can be Uncoupled Through Substitution of a Single Amino Acid BanLec is a potent inhibitor of HIV-1 infection and a prospect for microbicide development (Ferir et al., Antiviral Res 90, 200-204 2011; Swanson et al., J Biol Chem 285, 8646-8655 2010). To allow for the possibility of large-scale production and genetic alterations, a recombinant version of BanLec with a C-terminal 6×His tag (rBanLec) was engineered. The rBanLec protein was produced in *E. coli* and purified with yields similar to those described by others for a different recombinant BanLec isoform (Gavrovic-Jankulovic et al., The international journal of biochemistry & cell biology 40, 929-941 2008). Isothermal titration calorimetry showed no difference between BanLec and rBanLec in affinity for the ligand methyl α-d-mannopyranoside, indicating no alteration in binding capacity to the primary contact site. As a further control for ligand binding on the level of N-glycans, the anti-HIV-1 activities of the banana-derived and recombinant forms were compared. Recombinant BanLec inhibited HIV replication in the low nanomolar range (FIG. 7), illustrating that it maintained its potency as an antiviral agent.

Figure 8:
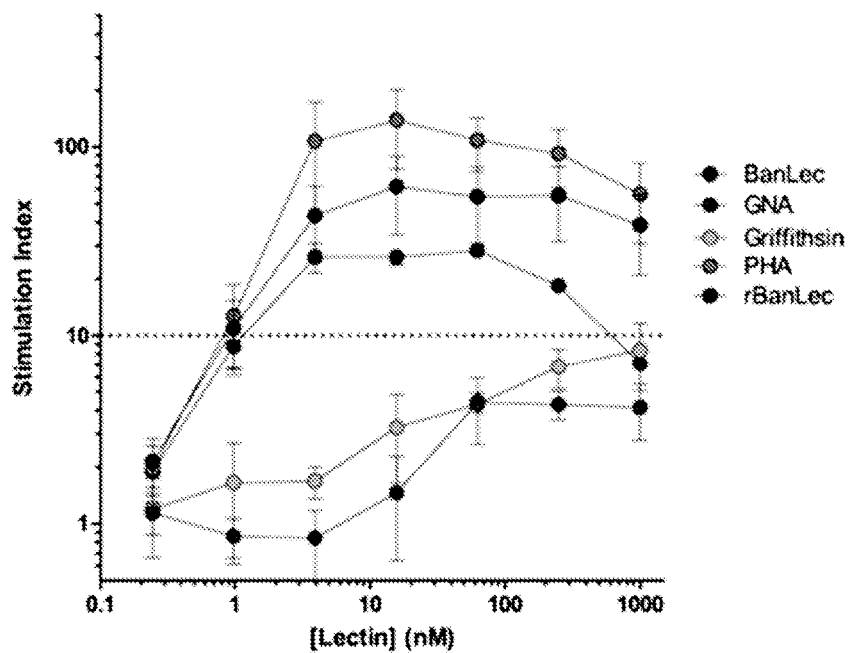
FIG. 8 shows a comparison of the mitogenic activity of BanLec to other lectins.

Two groups have reported naturally derived BanLec to be a mitogen (Gavrovic-Jankulovic et al., 2008 supra; Koshte et al., Biochem J 272, 721-726 1990). Therefore, BanLec was tested along with phytohaemagglutinins of known mitogenic properties to determine its relative activity and compare these results with data obtained for the recombinant form. PHA-L (the leuko-agglutinin from kidney beans) is a known mitogen and was used as a positive control, while GNA (*Galanthus nivalis* agglutinin) and Griffithsin, previously reported to be non-mitogenic, served as negative controls. Mitogenic activity was assessed by exposing peripheral blood lymphocytes (PBL) to various concentrations of lectin for three days prior to the addition of BrdU. The amount of BrdU incorporated into DNA by proliferating cells was determined, and the mitogenic activity was quantified as the stimulation index. This is the fold increase in signal of the treated sample versus the (mock-treated) control sample. High stimulation index values were observed in the presence of the known mitogen PHA-L. The values obtained for GNA and Griffithsin were found to be much lower than those observed for PHA-L, setting a standard for lack of stimulation. Explicitly, the observed stimulation index values were less than ten for these negative control lectins, so a value of less than ten was considered to be non-mitogenic. As shown in FIG. 8, the two preparations of BanLec clearly surpassed this threshold. These measurements therefore confirmed the status of these lectins as mitogens. The natural and recombinant proteins thus actively block viral infection (by N-glycan binding) and stimulate proliferation (by cell surface binding, counter receptor cross-linking, and induction of pro-proliferative signaling).

Using previously reported crystal structures of the natural BanLec, amino acids that could potentially influence the lectin's binding activity were first identified. BanLec has a β-prism I structure that is common to members of the Jacalin-related lectin (JRL) family to which BanLec belongs (Meagher et al., Glycobiology 15, 1033-1042 2005; Singh et al., Glycobiology 15, 1025-1032 2005). This folding consists of three Greek Key structures composed of 3-strands. Distinct loops found in the Greek Keys play a role in carbohydrate binding. The first and second Greek Keys include the JRL consensus motif GXXXD (SEQ ID NO:1) for binding, and therefore the first targets for engineering were these sites. When mutations were introduced into the first and second Greek Keys, they abolished the mitogenic activity (as seen with the D133G mutant shown in FIG. 1A), but also resulted in a loss of almost all anti-HIV activity. The third Greek Key varies among JRL members in terms of length and sequence, and is thought to play a role in binding glycan structures beyond simple saccharides (Nakamura-Tsuruta et al., Febs J 275, 1227-1239 2008). H84 is found in this third loop, and has been predicted to play a role in binding of the second sugar moiety in α1,6-dimannosides (Singh et al., 2005 supra). It was contemplated that altering this amino acid would result in a change in binding characteristics that would affect its mitogenic and antiviral activities differentially.

A panel of mutants of BanLec at H84 was constructed, systematically replacing the imidazole ring with other aromatic substituents, ionic, polar or aliphatic groups, and a hydrogen atom only in H84G. The mutant proteins were purified and tested for mitogenic and pro-inflammatory activity. Systematic testing revealed that one variant, H84T, in which the histidine is replaced by a threonine, did not stimulate the proliferation of lymphocytes at concentrations up to 1 μM (FIG. 1A). Comparison of the pro-inflammatory activity of the wild-type (WT) and the H84T mutant proteins was further extended by measuring presence of the activation marker CD69 on CD4$^+$ peripheral blood mononuclear cells (PBMC). Increased cell surface expression of CD69 was observed for BanLec-treated CD4$^+$ PBMC. In sharp contrast, the H84T variant induced very little upregulation of this activation marker, indicating that this mutation substantially reduces this protein's potential to stimulate mononuclear cells (FIG. 1B). Moreover, PBMC were isolated from multiple donors and it was tested comparatively whether cytokine/chemokine production was stimulated by WT BanLec or its H84T variant. Since the relative cytokine production among donors is inherently widely variable, cytokine responses were grouped over several intervals of production: 1-3, 3-10, 10-100, 100-500, and 500+ fold over background. WT BanLec consistently caused a large increase in the production of multiple cytokines. The H84T variant, in direct comparison to the effects of the WT protein, led to a markedly reduced production of cytokines (FIG. 1C). Thus, H84T BanLec, unlike naturally occurring BanLec, is minimally mitogenic.

Figure 2:
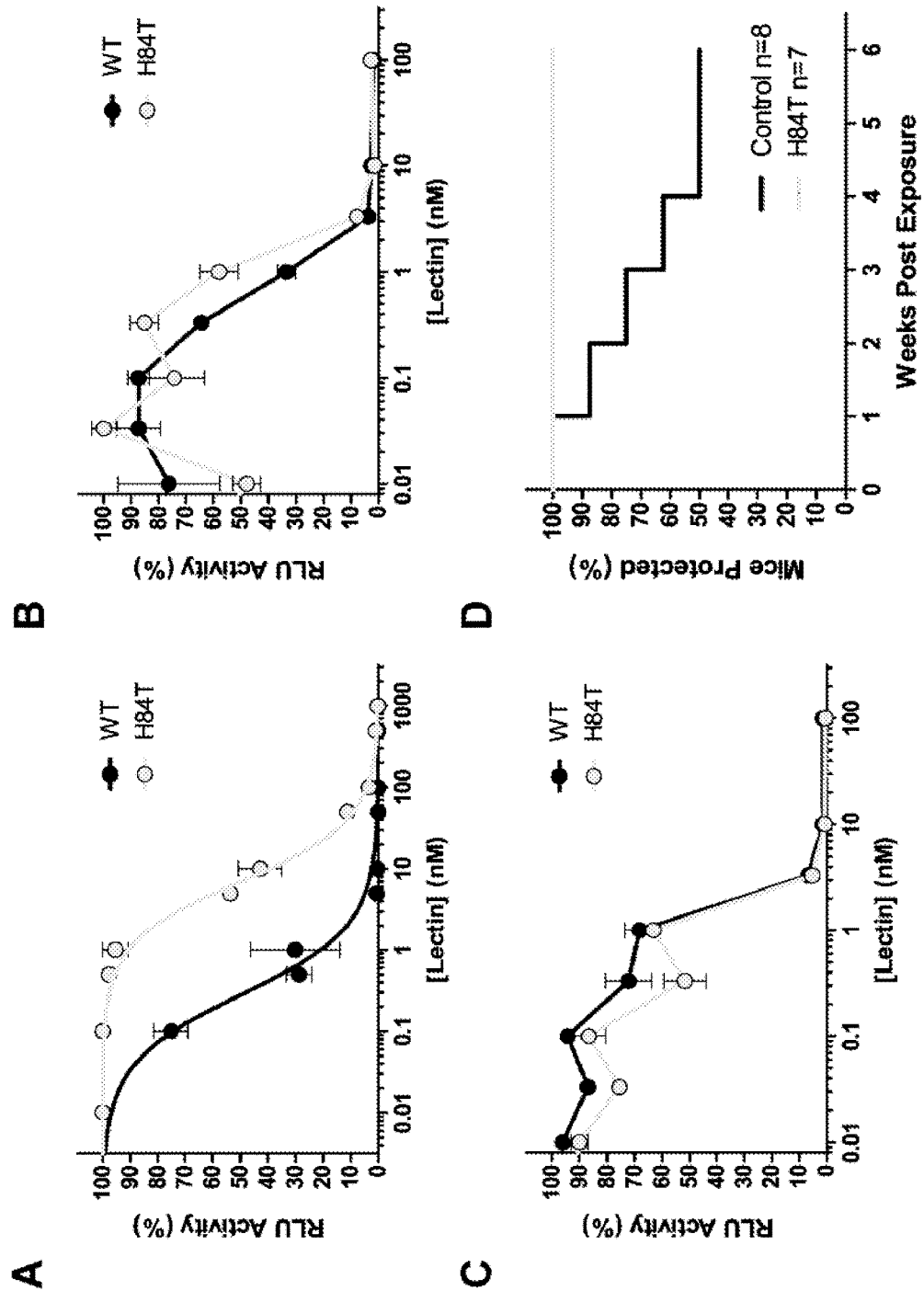
FIG. 2 shows that H84T BanLec has potent antiviral activity in vitro and in vivo. (A) TZM-bl cells were pretreated with different concentrations of WT BanLec or the H84T mutant for 30 minutes prior to infection with HIV-1 pseudo-typed virus containing a consensus subtype B envelope. (B) The activity of WT BanLec or the H84T mutant against the 1918 H1N1 pandemic influenza strain as measured by luciferase assay in the pseudo-typed virus system described in the Methods section. (C) The activity of WT BanLec and its H84T mutant against the H5N1 avian influenza strain as assessed in (B). (D) Protection from vaginal HIV-1JR-CSF infection of BLT humanized mice by H84T BanLec.

The loss of mitogenicity indicated that the H84T mutant protein finds use in vaginal microbicide and as a broad-spectrum antiviral agent, as many pathogenic viruses present high-mannose-type N-glycans on their surfaces. Indeed, it was found that the H84T variant, while showing a very modest loss of anti-HIV activity relative to WT protein, still had an $IC_{50}$ in the low nanomolar range (FIG. 2A). This inhibition was seen with multiple different isolates of HIV, and ranged from being equal to or within one log of that of WT BanLec. Of further medical relevance, as pandemic disease caused by influenza A virus is a major threat to global health, it was tested whether WT and mutant BanLec proteins could inhibit its replication. Since the haemagglutinin of influenza A viruses bears high-mannose-type N-glycans that are susceptible to host lectins (Collins and Knight, 1978 Glycobiology 15, 1033-1042; Ng et al., 2012 J Biomed Biotechnol 2012, 732191; Reading et al., 2000 J Virol 74, 5190-5197), this type of virus is another target for H84T BanLec. A test system (Temperton et al., Influenza and other respiratory viruses 1, 105-112 2007) was used in which a retroviral core is pseudotyped with the haemagglutinin of the influenza virus in question (kind gift of Dr. Gary Nabel). WT and H84T BanLec proteins were both very active and equally inhibited replication of both the 1918 H1N1 virus and the H5N1 avian influenza virus (FIG. 2B, C). In contrast, a large set of mutants, which we found to be of similar or lesser mitogenicity than H84T, were unable to inhibit HIV replication or had no effect against influenza, underscoring the difficulty of specifically knocking down one functional activity while retaining another. Therefore, the H84T mutant is a minimally mitogenic protein that finds use as an effective therapeutic agent against pandemic influenza, HIV, and other pathogenic viruses with a mannose-rich surface.

To determine the in vivo efficacy of H84T BanLec to prevent mucosal HIV transmission, the bone marrow-liver-thymus (BLT) humanized mouse model (Wahl et al., PLoS pathogens 8, e1002732 2012) was used. This system is a validated in vivo model for the analysis of HIV transmission and prevention strategies (Denton et al., J Virol 86, 630-634. 2012). When challenged vaginally, BLT humanized mice recapitulate key aspects of HIV-1 infection, including mucosal transmission, sustained viral replication and depletion of CD4$^+$ T cells. H84T BanLec or PBS (the carrier) were topically applied to the vagina prior to challenge with HIV-1$_{JR-CSF}$. Fifty percent of the mice treated vaginally with PBS only became infected, as determined by the presence of viral RNA in the plasma. In contrast, none of the mice treated topically with H84T BanLec showed detectable levels of viral RNA in the plasma during the course of the experiment (p=0.0359; FIG. 2D). Thus, the newly engineered BanLec variant H84T has significant antiviral activity in vitro and in vivo. Of particular note, it lacks the mitogenic capacity of the WT protein, fulfilling the stringent prerequisites of the test model as outlined above. In order to elucidate why mitogenicity had been largely uncoupled from antiviral activity in H84T BanLec, the proteins were tested for carbohydrate binding activity, with free sugar and glycoclusters, the latter used as tools to characterize lectin reactivity to high-density ligands.

H84T BanLec is Less Active in Multivalent Interactions

Figure 9:
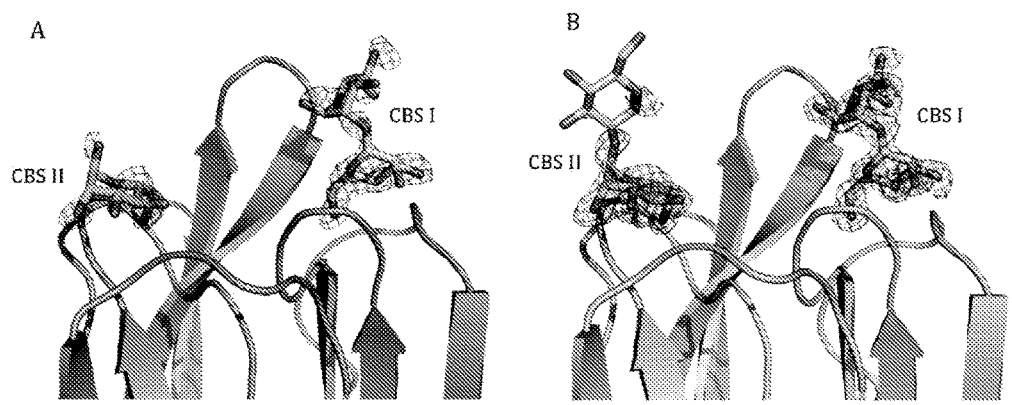
FIG. 9 shows electron density maps of dimannose bound to WT BanLec in blue (A) and to the H84T mutant in yellow (B).

To delineate of the structural basis of the H84T mutant protein's markedly decreased mitogenic and pro-inflammatory activity, while maintaining its potent antiviral capacity, the binding properties of H84T and WT BanLec in solution were compared. Using isothermal titration calorimetry, $K_D$-values for methyl α-d-mannopyranoside and for mannobiose were found to be similar for rBanLec and H84T (Table 1 below). The H84T mutant protein was crystallized. The crystal structure of H84T BanLec loaded with mannose showed no significant structural differences in the WT protein's structure (FIG. 9). No effect of the mutation on binding of the mono- and disaccharide or the lectin's crystal structure on a global level could be detected.

As mitogenicity is thought to involve cross-linking of distinct counter receptors on cell surfaces to trigger outside-in signaling, the profound loss of mitogenicity seen with the H84T BanLec and its conserved ability to efficiently bind its cognate monosaccharide indicated that the biological differences between the two proteins might depend on their reactivity to complex glycans. A simple assay that provides insights into binding to cell surface glycans and cross-linking activity (here in trans, that is between cells) is measuring lectin-induced aggregate formation of erythrocytes. The ability to agglutinate rabbit red blood cells is common among mannose-specific lectins, based on targeting mannosides and cross-linking determinants in bi- to multivalent fashion to form cell aggregates. When tested for this property, the minimal concentrations for agglutination were conspicuously different, at 3 μg/mL and 437 μg/mL for rBanLec and H84T, respectively (Table 1). This result reveals a marked difference in building stable aggregates based on more than monovalent interactions with cell surface mannosides. To further examine this aspect, synthetic glycoclusters are excellent tools, which range in size from bivalent compounds to glycodendrimersomes (Chabre and Roy, 2009, 2010 Fundamentals of glycosciences, H. J. Gabius, ed. (Weinheim, Wiley-VCH), pp. 53-70; Adv Carbohydr Chem Biochem 63, 165-393; Murphy et al., 2013 Molecules 18, 4026-4053; Percec et al., J Am Chem Soc 135, 9055-9077 2013). Their locally increased density of ligands will trace a change in the interaction/association profile when testing WT and variant proteins under identical conditions.

The association of a lectin with a ligand-bearing surface is sensitive to the presence of haptenic sugar, and its presentation in local clusters can enhance its inhibitory capacity. Mimicking the natural display of high-affinity ligands, synthetic glycoconjugates (carbohydrates attached to a scaffold enabling oligo- to polyvalency) thus are potent tools to determine reactivity profiles to cell surface-like topologies in quantitative terms (Chabre and Roy, 2009 supra; Gabius, 2001 Anatomia, histologia, embryologia 30, 3-31; Lee, 1994 Neoglycoconjugates Preparation and Applications, Y. C. Lee, and R. T. Lee, eds. (San Diego, Academic Press), pp. 23-50). The design of glycoclusters and the determination of their inhibitory activity on lectin binding, measured as the inhibitory concentration (IC) at which the extent of lectin binding to a glycoligand is reduced by 50% ($IC_{50}$-value), provide a measure of the avidity of multivalent associations. In total, a panel of 11 bi- to dodecavalent glycoclusters were tested systematically in titrations in two types of assay, one biochemical and one cellular. In both cases, the mannose-specific lectin concanavalin A was used as positive control, and lectin binding to the glycan-presenting matrix was ascertained to be saturable and dependent on carbohydrate presence.

Figure 3:
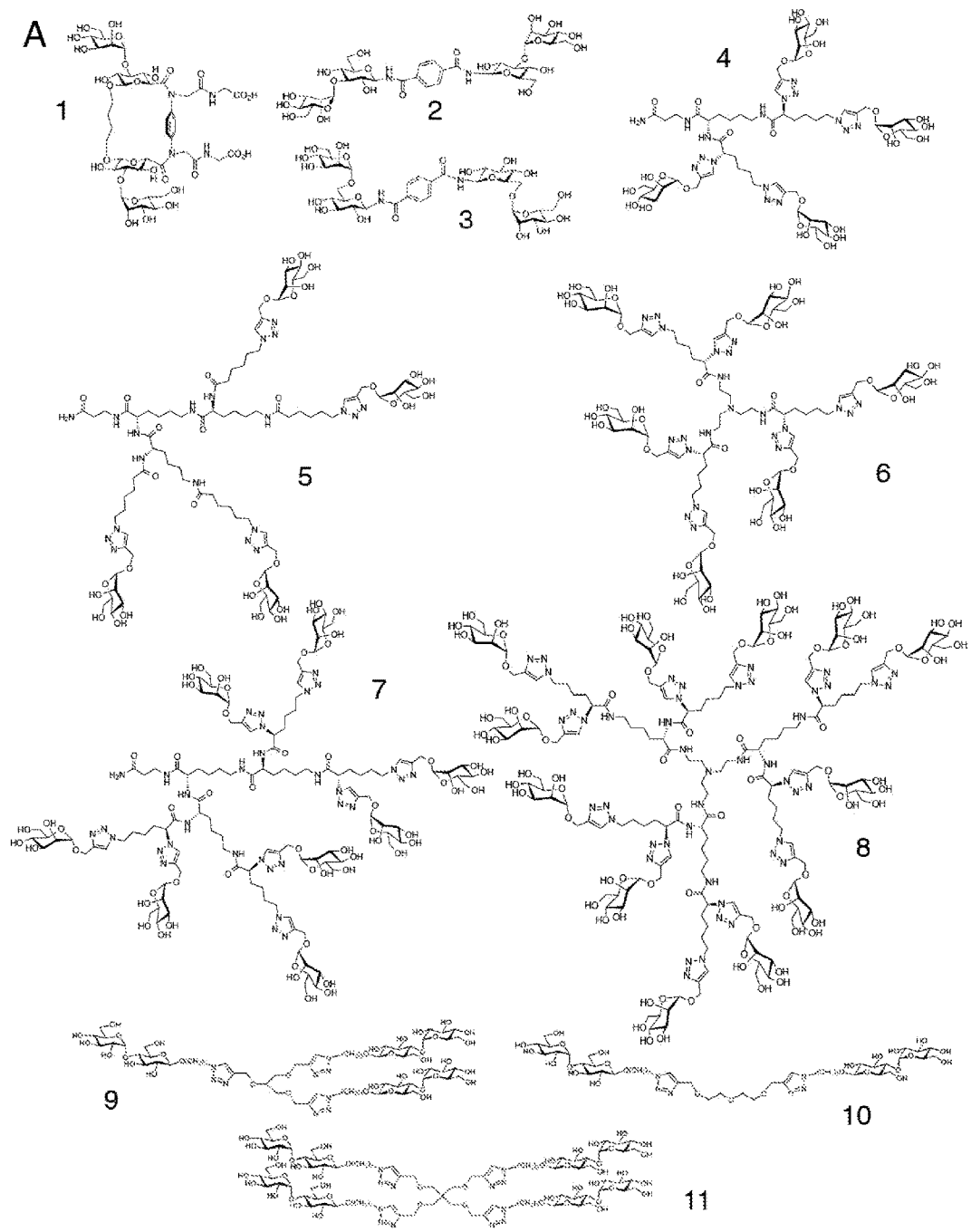
FIG. 3 shows binding of H84T and WT BanLec to glycoclusters. (A) Structures of the tested glycoclusters. (B) Titration curves for relative signal intensity reflecting extent of binding of the WT and H84T mutant BanLec proteins to surface-immobilized neoglycoprotein in the presence of increasing amounts of the tetravalent maltose-presenting glycocluster. (C) Semilogarithmic illustration of fluorescent surface staining of human SW480 colon adenocarcinoma cells by labeled WT (left panel) or H84T (right panel) BanLec.
Figure 3:
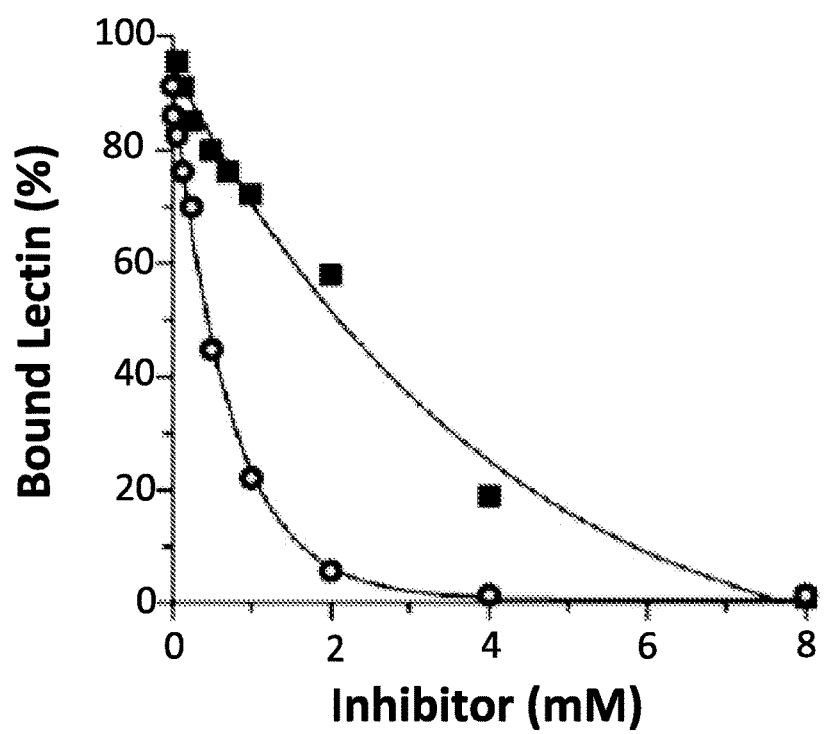
Figure 3:
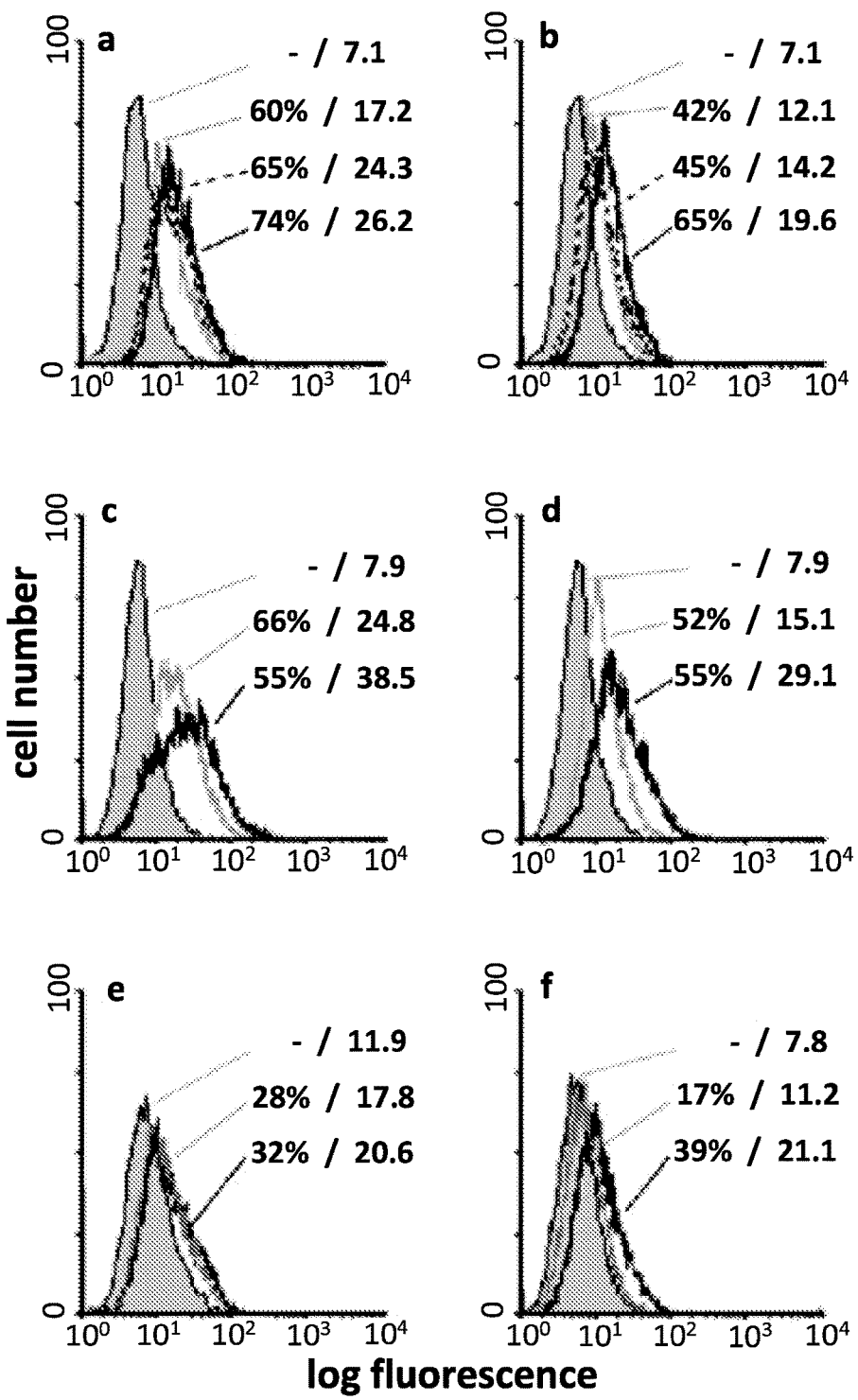

In the first system, a surface rich in presentation of mannose residues was established. A neoglycoprotein (a conjugate of albumin and mannose derivatives) was adsorbed to the plastic surface of microtiter plate wells, building the matrix for letting the biotinylated lectins dock. Surface-associated label was then quantitatively assessed spectrophotometrically, using a chromogenic reporter system. Titrations of the extent of binding with increasing amounts of inhibitor were performed to determine the $IC_{50}$-value. FIG. 3 shows binding of lectins to glycoclusters. The glycoclusters (bivalent phenylenediamine-based glycocylophane (1) and terephthalamide-based compounds (2, 3), mannose-presenting tetra- to dodecavalent glycoclusters (4-8) and maltose-containing bi- to tetravalent glycoclusters based on propargyl-derivatized alcohols 9-11) (André et al., 2010 Mol Pharm 7, 2270-2279; André et al., 2003 Org Biomol Chem 1, 3909-3916; André et al., 2009b Org Biomol Chem 7, 4715-4725; Papadopoulos et al., 2012 Mol Pharmaceut 9, 394-403) (FIG. 3A) were individually tested. As can be seen in the example shown in FIG. 3B, these experiments allowed one to determine $IC_{50}$-values as a measure for sensitivity of lectin binding in the presence of inhibitors. Binding of the H84T mutant was found to be much more susceptible to glycocluster inhibition than was the WT lectin (Table 2, below).

To address the possibility that the above observations may be biased by the characteristics of the solid-phase system and to increase the biological relevance of the findings, cell binding was monitored using the surface of cultured cells as a platform for contact of the labeled lectins. Tested under identical conditions, the WT lectin reacted more strongly than the H84T mutant did with cells (FIG. 3C a,b). In addition to testing the physiologic glycome profile on the cells, the level of lectin-reactive high-mannose-type N-glycans was increased by treating the cells with the α-mannosidase I inhibitor 1-deoxymannojirimycin. Comparative analyses revealed enhanced binding of both proteins (FIG. 3C c,d), with the difference in mean fluorescence intensity between the H84T variant and the WT protein being maintained. Thus, upregulation of ligand availability did not reduce the relative difference between H84T and WT proteins. Glycocluster testing on cells, for example the tetravalent compound 11 (FIG. 3C e,f), confirmed the differential sensitivity seen in the solid-phase assays. Thus, the presence of glycoclusters can reduce the extent of binding of the H84T mutant protein to multivalent surfaces more readily than that of the WT BanLec protein, consistent with the observation of decreased capacity for agglutination of erythrocytes. The reactivates of the two proteins to multivalent surfaces, but not to the monosaccharide, were thus different. A detailed analysis of the protein structures was performed to understand the differential recognition of clustered glycans by H84T and WT BanLec.

High Resolution X-Ray Structures Reveal the Loss of Pi-Pi Stacking Between Y83 and H84 and Altered Sugar Binding Specificity in H84T The observation that the reactivity profiles of WT and H84T BanLec protein to glycoclusters differed indicated that structural modifications resulted from introducing the mutation that could impact the way the proteins bind natural glycans. To examine this hypothesis on the atomic level, the crystal structures of both the recombinant WT and the H84T variant proteins were determined (FIG. 4A). As indicated above, the monomer of BanLec is a β-prism I fold containing three Greek Key motifs with 3-fold symmetry and two carbohydrate binding sites. Carbohydrate binding site I (CBS I) consists of loops on the top of the first Greek Key; carbohydrate binding site II (CBS II) is on the top of the second Greek Key. Separating the two binding sites is a loop (residues 83-88) from the third Greek Key (FIG. 4A), which has been indicated to be an important determinant of specificity (Meagher et al., 2005 Glycobiology 15, 1033-1042); H84 is within this loop. Glycerol units were observed in the different binding sites. Although there is very little difference in the overall backbone positioning of the apo structures, as indicated by an RMSD of 0.262 Å, the H84T mutation results in subtle structural changes in the sugar binding region. In the WT protein, H84 forms a pi-pi stacking interaction with Y83, directing both bulky residues toward CBS II. In the H84T mutant, the absence of this pi-pi stacking allows the threonine side chain to point towards CBS I. The presence of the imidazole involved in the pi-pi stacking in the WT protein allows for a better separation of the two binding sites by simultaneously serving as a wall between the two sites, increasing the rigidity of the third Greek Key, and disfavoring the coupling between the two sites allowed by the re-orientation of the threonine in the H84T mutant. This indicates that the third Greek Key could act as a wedge between the two binding sites in the WT protein, and its alteration in the H84T mutant could be the structural origin of the different levels of mitogenic activity of the two proteins.

Figure 4:
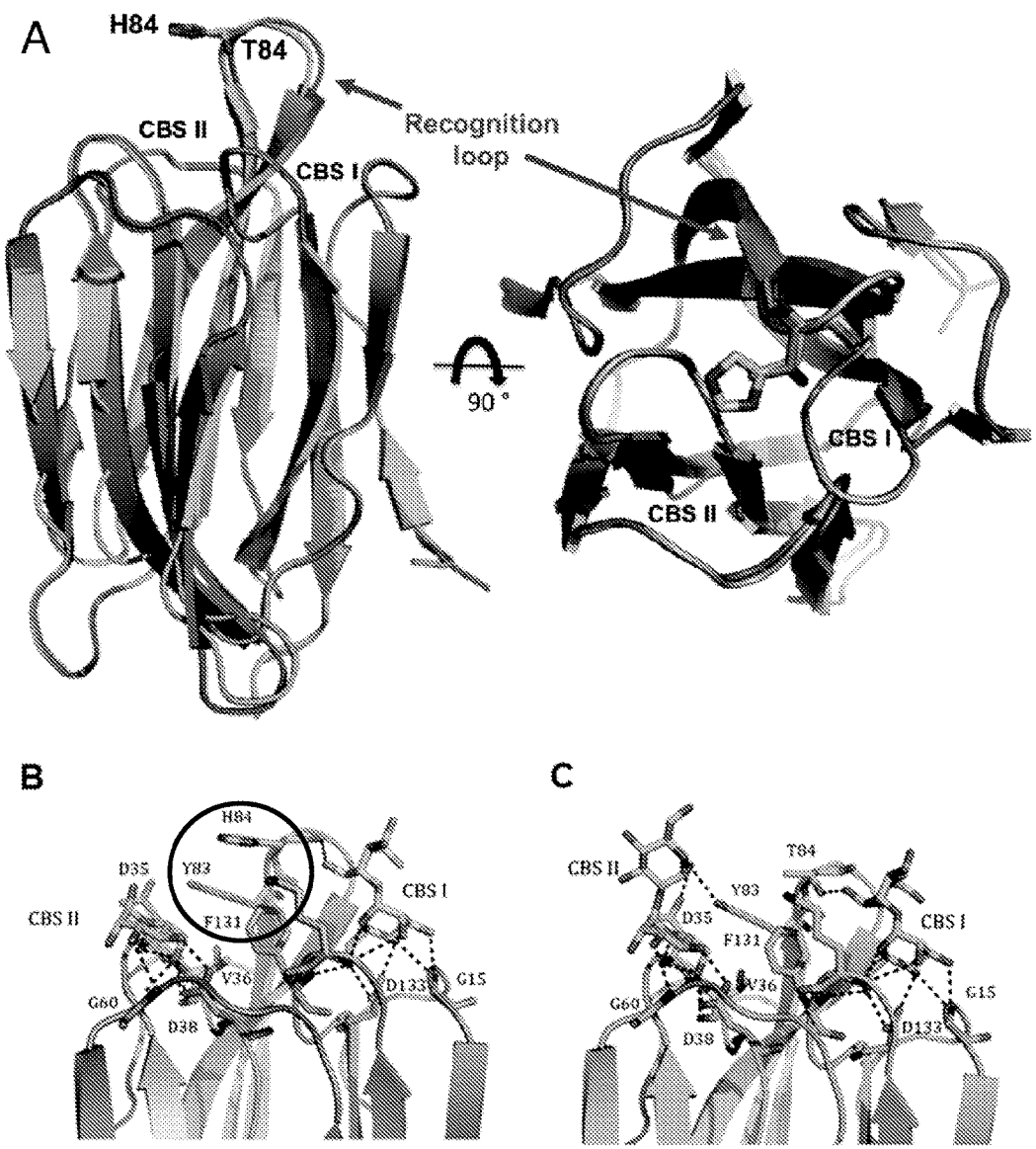
FIG. 4 shows a comparison of crystal structures of recombinant WT BanLec and its H84T mutant. (A) Overlay of the structures of a monomer of recombinant WT and H84T BanLec. (B,C) Binding of a dimannoside to WT BanLec (B) and to the H84T mutant (C).

To determine effects that the H84T mutation exerts on ligand binding crystallographically, the crystals of both WT and H84T proteins were soaked in a solution containing dimannoside (M2). In these crystals, there are two dimers in the asymmetric unit, which results in four sets of CBSs. The procedure led to loading of binding sites. The position of the first mannose unit of M2 is well resolved in the electron density maps of CBS I & II of both proteins, indicating that it is tightly bound to both structures (FIG. 4B, C and FIG. 9). In CBS I of the WT and H84T proteins, there are five hydrogen bonds (H-bonds) between each protein and the first mannose residue, involving OD1 and OD2 of N133 and the backbone N of G15, K130, and F131. In CBS II, there are six H-bonds stabilizing the position of the saccharide, which include side chain atoms, OD1 and OD2, of N38 and the backbone N of N35, V36 and G60.

The main difference in ligand binding between the proteins involves residue 84 and the second saccharide unit that is more accessible to solvent. This mannose residue gives visible density in CBS I for three out of four chains of the WT protein and all four chains of the H84T protein, but is present in the CBS II for only one H84T chain. For the CBS I site, each protein makes one H-bond with the saccharide unit.

In the WT protein, H84 does not form strong interactions with the sugar in the CBS I pocket (FIG. 4B), while in the mutant structure, the side chain of T84 swings into the CBS I pocket to form a H-bond with this O1 hydroxyl oxygen of the sugar (FIG. 4C). The existence of pi-pi stacking locks the imidazole ring of H84 towards the CBS II and its loss in the H84T mutant allows for this reorientation towards the CBS I. Thus, although the global structures of WT and H84T BanLec proteins are not markedly different as assessed by crystallography, the loss of pi-pi stacking alters the intermolecular sugar-protein contact profile and topological presentation of the sugar binding site, providing the first structural insights into the basis for the difference in the biological behavior between WT BanLec and its H84T mutant.

Figure 5:
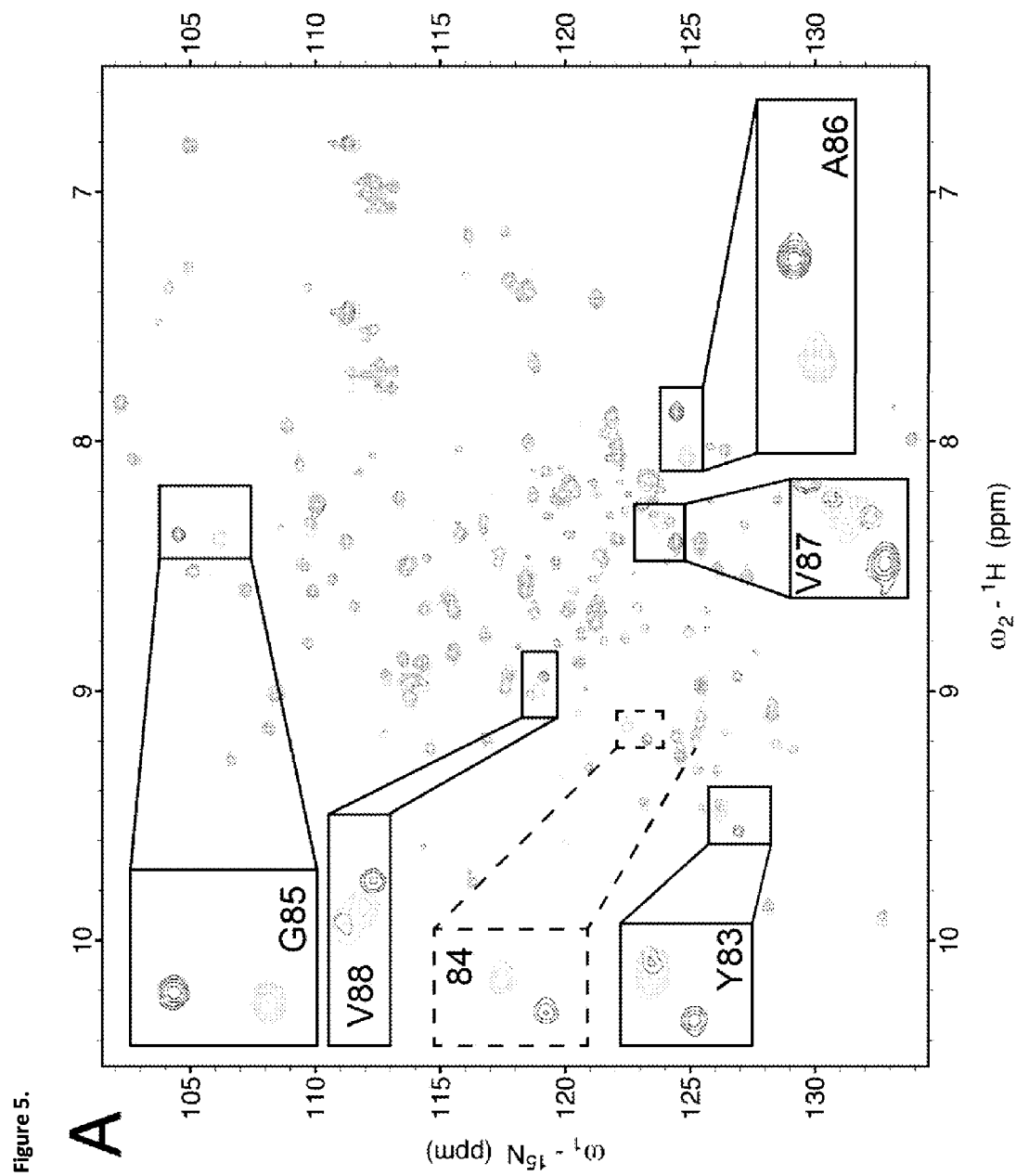
FIG. 5 shows that solution NMR spectroscopy reveals dynamic differences in the conformations of WT and H84T BanLec at the third Greek Key. (A) Comparison of H84T mutant and WT BanLec. $^{15}$N-$^{1}$H HSQCs of WT (blue) and H84T BanLec (yellow). (B) Chemical shift changes induced by the H84T mutation color-coded on the structure of WT BanLec. (C) Chemical shift changes upon pentamannose binding color-coded on the structure of WT BanLec. (D) Chemical shift differences between H84T and WT BanLec when interacting with sugar color-coded on the structure of WT BanLec.
Figure 5:
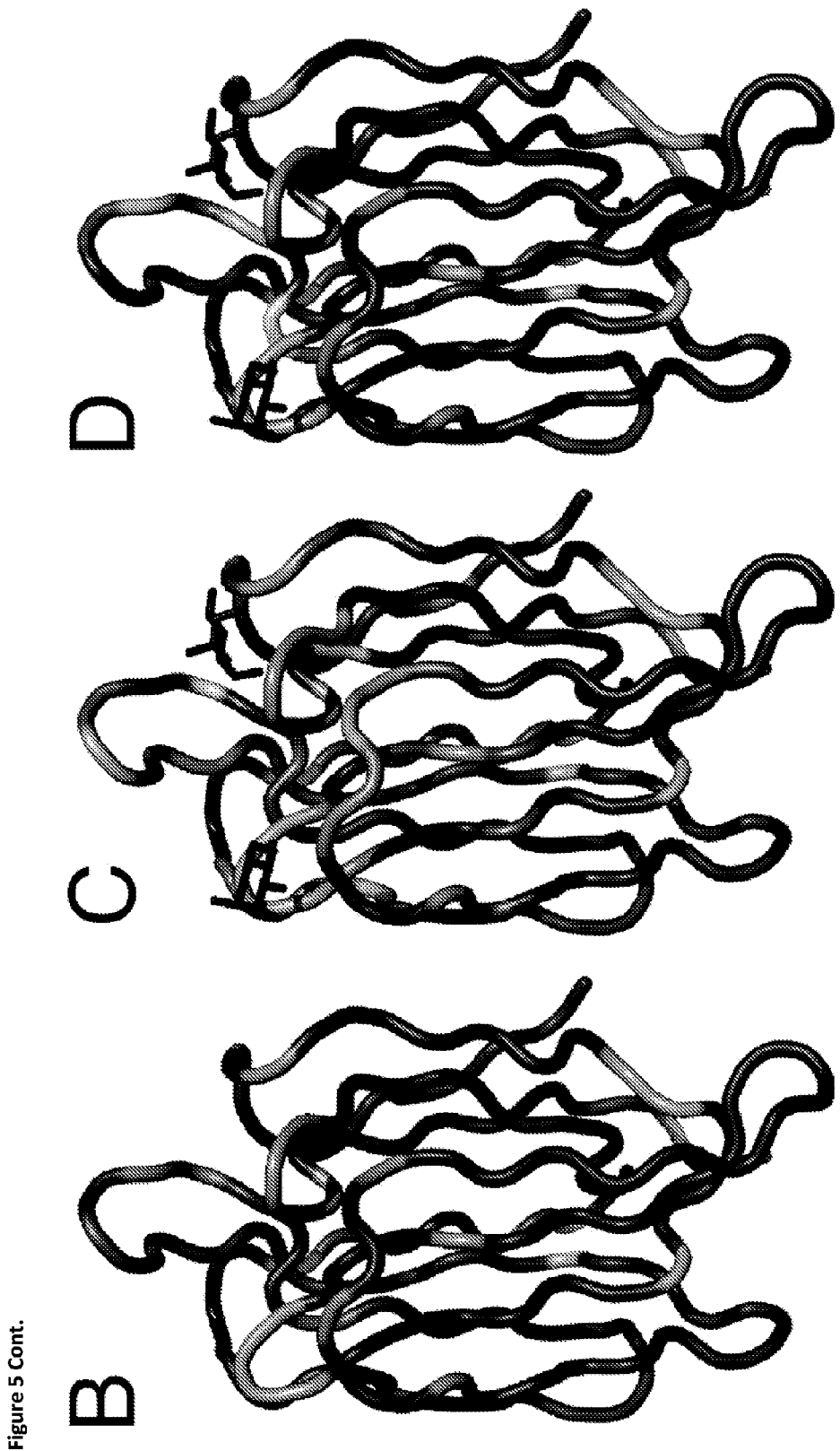
Figure 6:
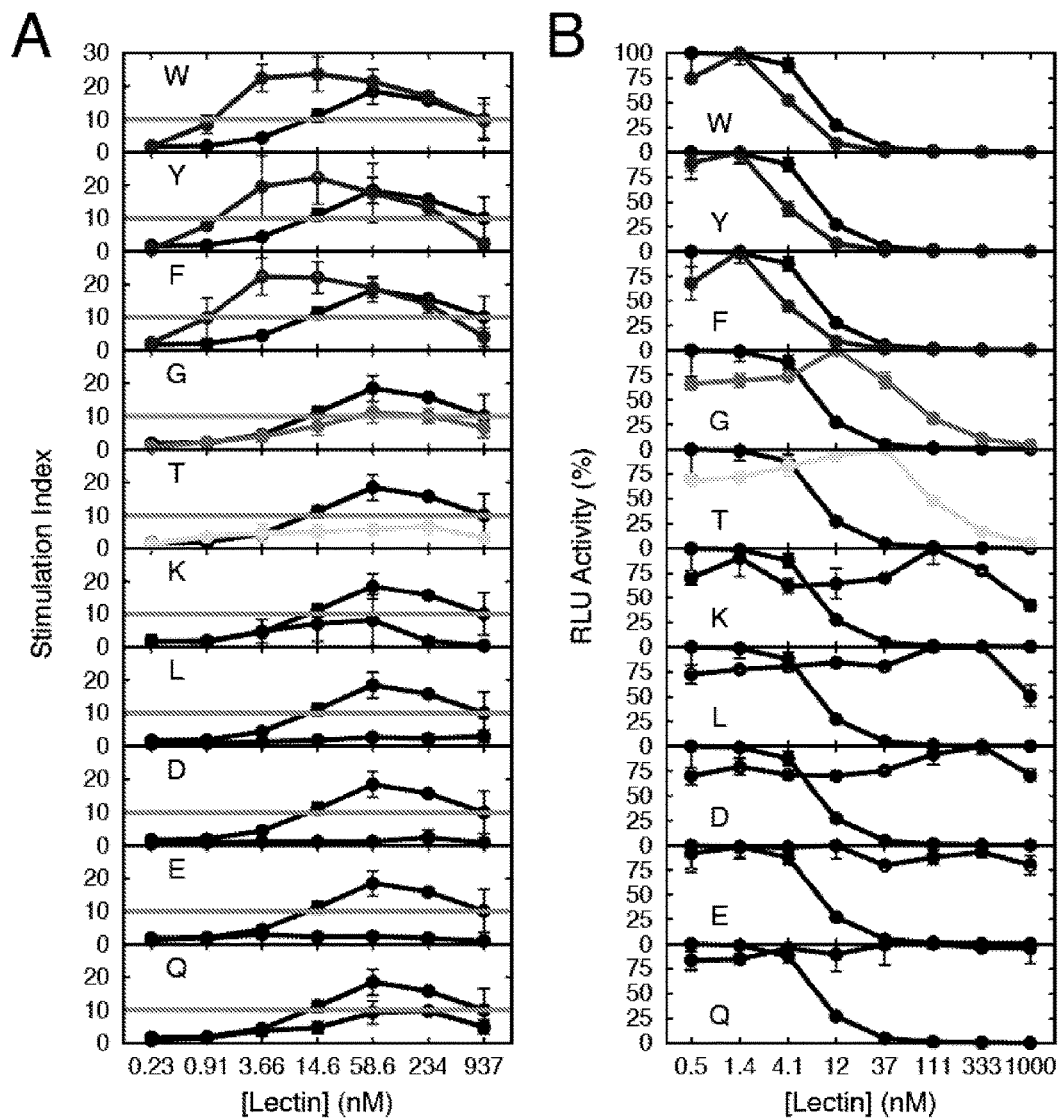
FIG. 6 shows that specific NMR shifts correlate with mitogenicity. (A) Comparison of the mitogenic activity of 10 types of H84X mutants to WT BanLec. (B) Antiviral activity of the same BanLec mutants. (C) Comparison of distinct chemical shifts of four representative H84X mutants of BanLec.
Figure 6:
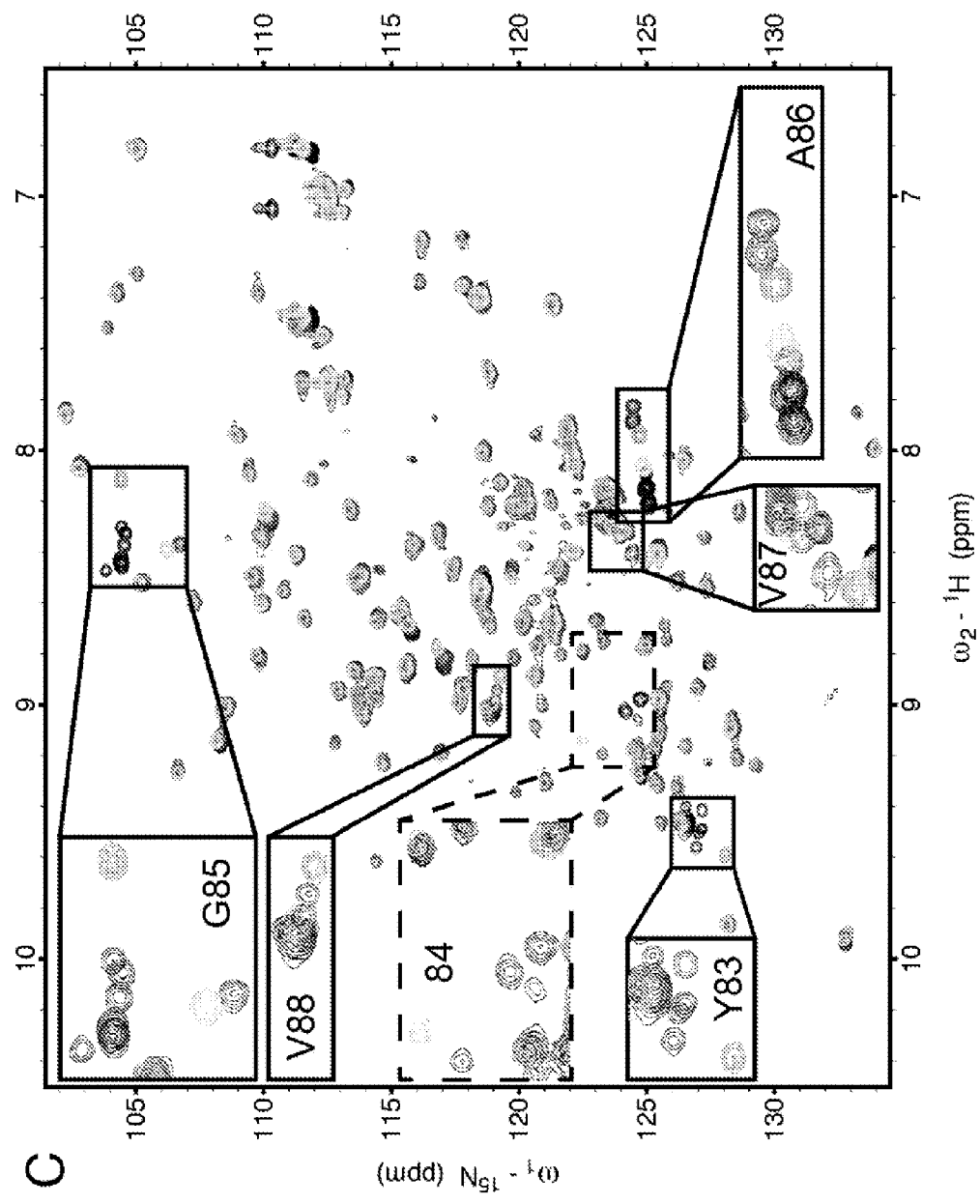

NMR Spectroscopy Reveals Dynamic Differences in the Structure of WT and H84T BanLec Solution-state NMR spectroscopy was used to further delineate differences between the conformational properties of WT and H84T BanLec. In agreement with the high degree of similarity seen between WT BanLec and H84T mutant in the crystal structures, significant spectral overlap was observed when comparing the 2D $^{15}$N-$^1$H HSQC spectra of BanLec and H84T (FIG. 5A). However, differences in chemical shifts are observed for several resonances, indicating that while the H84T mutation does not affect the overall fold of the protein, it does introduce structural and/or dynamic perturbations at specific sites.

Figure 10:
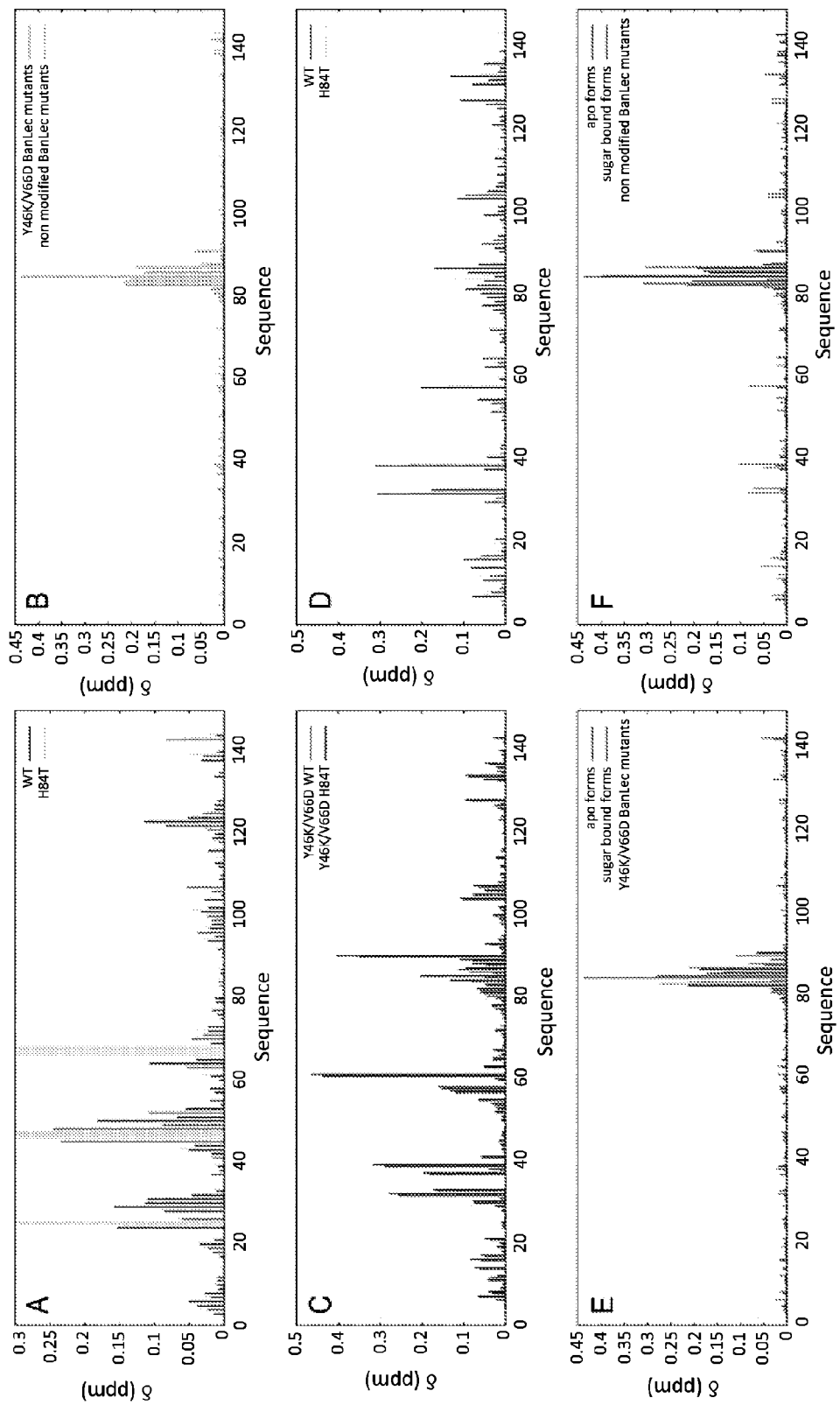
FIG. 10 shows a comparison of chemical shift profiles for H84T and WT BanLec. (A) Chemical shift changes between WT and Y46K/V66D double mutant of BanLec (blue) and the H84T and Y46K/V66D double mutant of H84T (yellow). (B) Chemical shift changes between WT and H84T (turquoise) and their double mutant versions (magenta). (C) Changes in chemical shift upon pentamannose binding for double mutant versions of WT BanLec (green) and H84T BanLec (red). (D) Changes in chemical shift upon dimannose binding for WT BanLec (blue) and H84T (yellow). (E) Comparison of the CS distance between WT and H84T double mutant with (olive) and without (brown) pentamannose. (F) Comparison of the CS distance between WT and H84T with (olive) and without (brown) dimannose.
Figure 11:
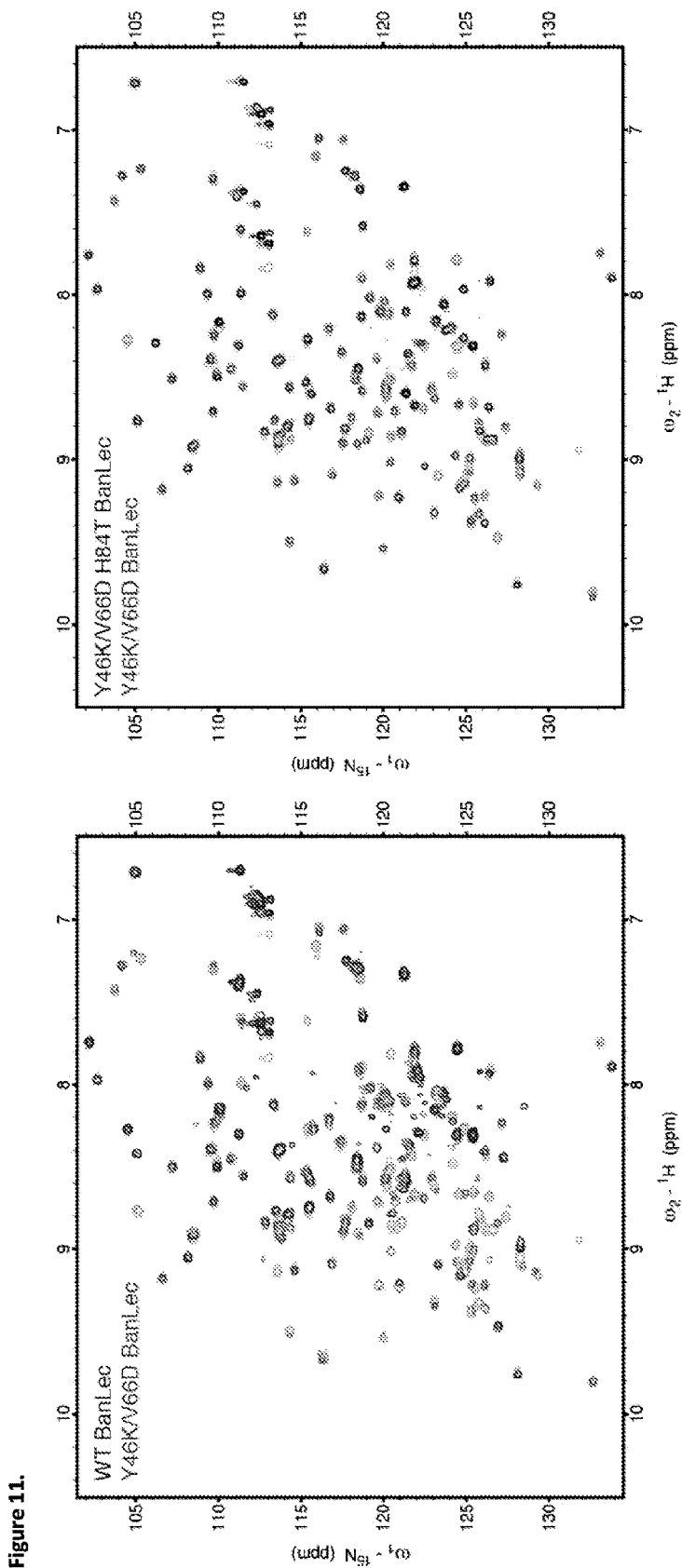
FIG. 11 shows a comparison of the $^{15}$N-$^{1}$H HSQCs of the different mutants of BanLec.
Figure 11:
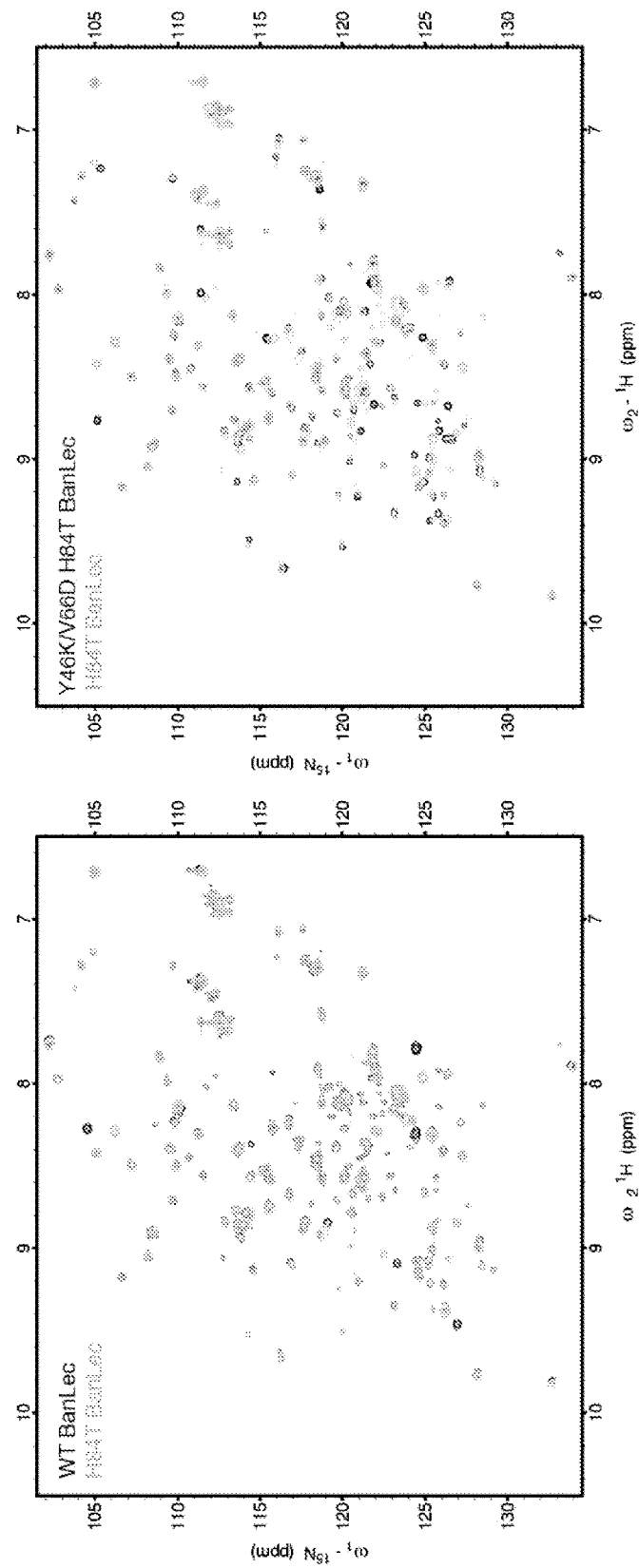
Figure 12:
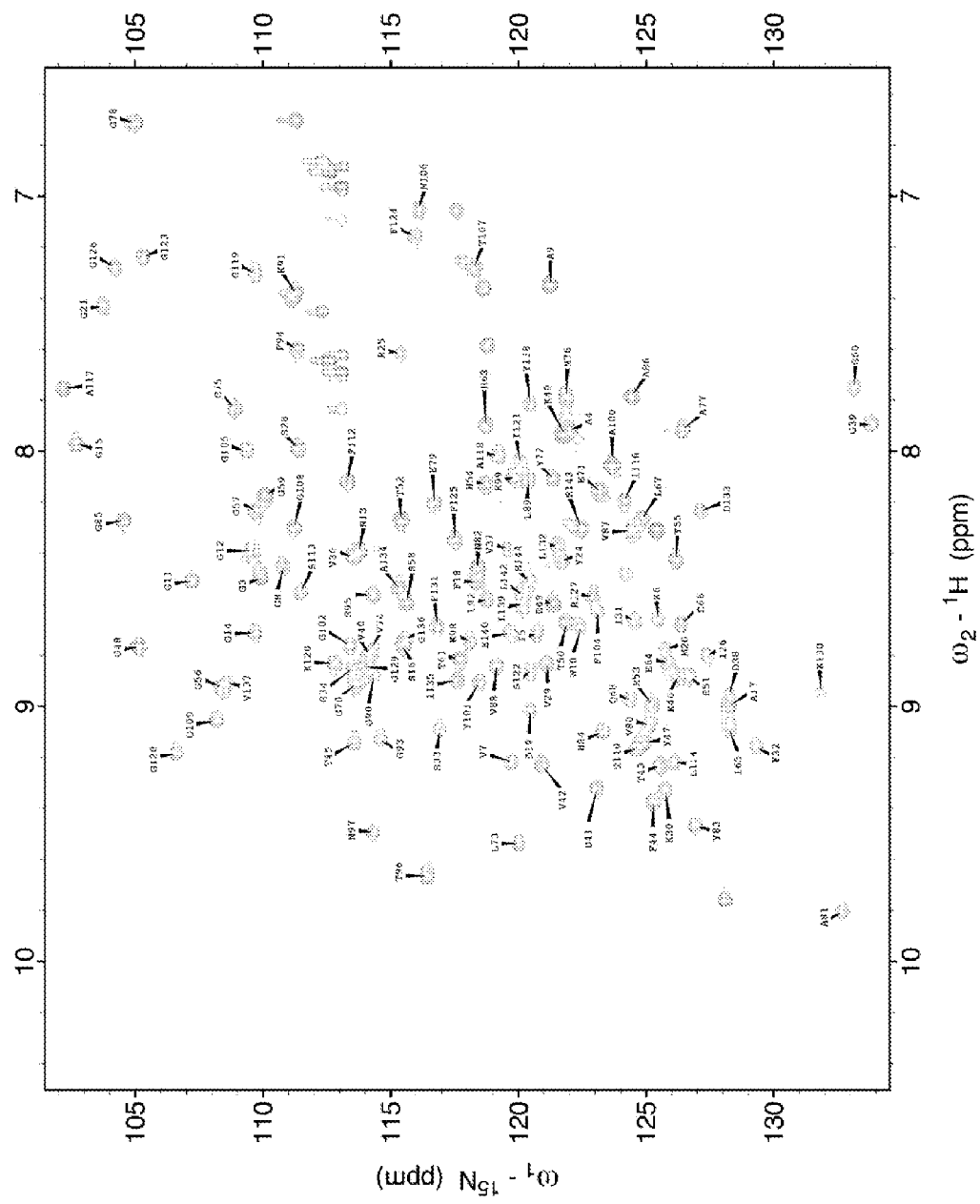
FIG. 12 shows assigned $^{15}$N-$^{1}$H HSQCs of the Y46K/V66D BanLec double mutant.
Figure 13:
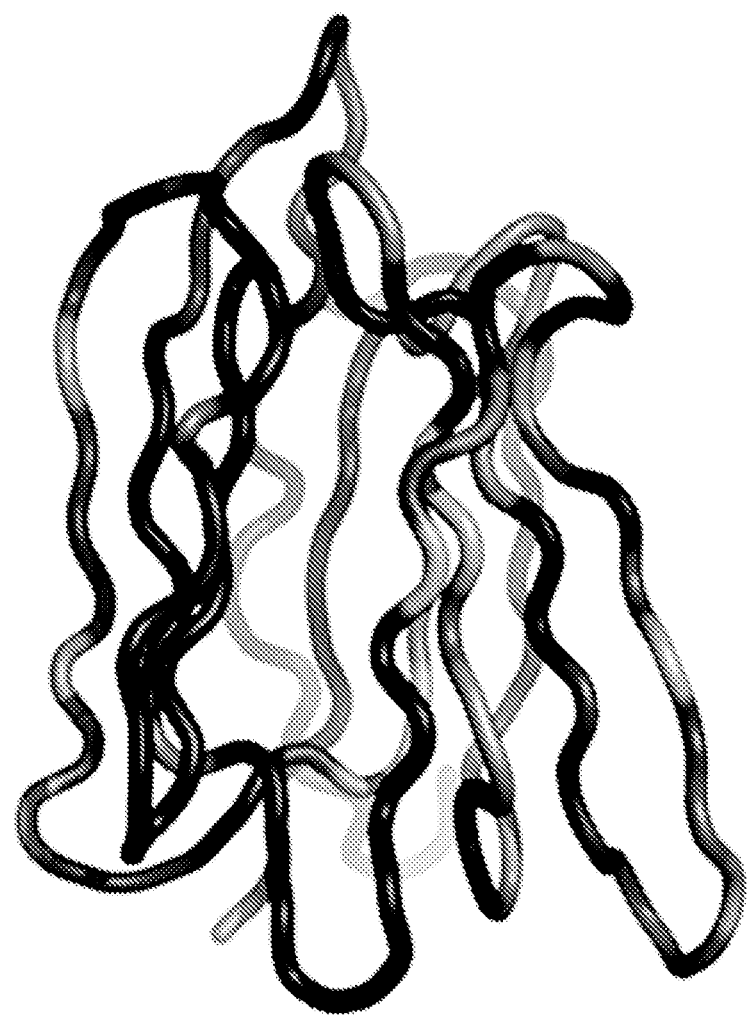
FIG. 13 shows chemical shift changes induced by the double mutation (Y46K/V66D) color-coded on the structure of WT BanLec.

Both WT and H84T BanLec exhibited a tendency to aggregate over time, which precluded application of multi-dimensional NMR experiments for assigning resonances (Sattler et al., 1999 Prog NMR Spectrosc 34, 93-158). The quaternary structure in solution may cause such a behavior. To overcome this problem, mutations designed to disrupt the tetramer interface between the two dimers were introduced. Based on the crystal structures, a Y46K mutant that disrupts a hydrophobic patch at the tetramer interface by substituting one of its hydrophobic side chains with a charged residue was designed. While the Y46K mutant formed the expected dimer as measured by $^{15}$N NMR spin relaxation, aggregation was still observed over time. A second mutation, V66D, was then introduced to increase the long-term solubility of the lectin. This double mutant (Y46K/V66D) yielded a dimeric protein with low propensity for aggregation. Its NMR spectra were very similar to those for WT BanLec (FIGS. 10A and 11). This mutant was used to carry out multidimensional resonance assignment experiments (Sattler et al., 1999 supra), allowing for ~93% of the backbone resonances to be assigned (FIG. 12). As most sections of the spectra were virtually identical, the transfer to the new double mutants was straightforward except in the vicinity of the double mutation (see FIGS. 10A and B), enabling a final overall assignment percentage of 89%. Full assignment of the three Greek Key regions was accomplished, as the chemical shift perturbations due to the double mutation were clearly localized on the other side of the protein (FIG. 13). The validity of assignment transfer was further rigorously confirmed by running an extensive program with mutations of residues in and around the sugar binding sites (A9G, D35E, K130R, D35K, F131Y, K130Q, N82T, A86G, D38G, K130G, T107S, V36G, A81G, D133E).

The chemical shift differences observed between the WT and H84T proteins are localized in the vicinity of the ligand recognition loop (residues 83-88) (FIG. 5B and FIG. 10B). Thus the effect of the mutation does not propagate over the entire sugar binding pocket but rather is mainly confined to the third Greek Key. The fact that chemical shift differences are observed throughout the entire loop suggests that the mutation modifies its structural and/or dynamic properties. The changes in chemical shift indicate an increase in flexibility of this region, as most of the chemical shift of residues 83 and 85-87 (including the largest two observed shifts, $^{15}$N of G85 and $^1$H of A84) of the H84T mutant come closer to the expected random-coil value of those residues than do the one observed in the WT protein (Kjaergaard and Poulsen, 2011 J Biomol NMR 50, 157-165). A change in dynamic properties in this region is contemplated based on the loss of the stabilizing pi-pi stacking interaction observed in the X-ray structure. This modulation in conformational plasticity of the sugar binding region could alter binding to high-mannose-type N-glycans and explain the differences observed between WT BanLec and its H84T mutant in glycocluster based studies and in mitogenicity assays.

Next, NMR chemical shift titrations were performed to investigate the interaction between WT BanLec and its H84T mutant with di- and pentamannosides in solution. Previously, trNOE experiments had revealed conformer selection of tri- to heptasaccharides by BanLec (Clavel et al., 2007 Eur J Org Chem, 1577-1585). The addition of dimannose to solutions with WT and H84T mutant proteins and of pentamannose to the respective Y46K/V66D mutant version of the two proteins resulted in significant chemical shift perturbations for residues in and around the sugar binding pocket defined by the X-ray structure (see FIG. 5C and FIGS. 10C and D). Several resonances belonging to residues in the sugar binding site also disappear (G59, K130 and F131), a process due to chemical exchange (Palmer, 2004 Chemical reviews 104, 3623-3640). The distribution and sites of the chemical shift changes are very similar between WT and H84T proteins, with the magnitude of chemical changes tending to be slightly larger for the H84T mutant when interacting with pentamannose (see FIG. 5D and FIGS. 10E and F). Once again, despite the similarities in the sugar induced perturbations for H84T and WT proteins, differences in magnitude are observed for residues belonging to the third Greek Key. These resonances show larger magnitude perturbations in the H84T mutant than in the WT protein, indicating that the third Greek Key exhibits a higher level of reorganization upon sugar binding, consistent with having a rigidifying "wall" in the WT protein that would tend to decrease the broadness of the conformational sampling in the absence of sugar. These data indicate similar sugar binding modes for WT and H84T proteins outside of the third Greek Key and persistence of any structure/dynamic differences seen in the apo form in sugar-loaded protein. The ability of the H84T mutant to efficiently bind the monosaccharide, but less so oligosaccharides, as compared to WT BanLec, indicates that the mutation disrupts the ability to structurally coordinate the different Greek Keys, either due to differences in the topological presentation of the sugar binding sites or due to a potentially higher degree of re-organization of the third Greek Key upon binding to the H84T mutant.

Specific NMR Chemical Shifts Correlate with Mitogenicity

To further explore the correlation between BanLec conformation and biological activity, an extensive mutagenesis approach was used: H84 was systematically substituted by amino acids that have different abilities to form stacking interaction. Replacing H84 with the aromatic residues tryptophan (H84W), tyrosine (H84Y), and phenylalanine (H84F) had minimal effects on mitogenicity and anti-HIV activity, all mutants enabling pi-pi stacking (FIG. 6). However, replacement of the imidazole by ionic, polar, or aliphatic side chains, including the amino acids lysine (H84K), aspartic acid (H84D), glutamic acid (H84E), glutamine (H84Q) and leucine (H84L), resulted in marked loss of both mitogenicity and anti-HIV activity (FIG. 6). The only mutation that yields a reasonably similar drop in mitogenicity as H84T while preserving some antiviral HIV activity is glycine (H84G). This rare occurrence of a favorable outcome underscores the difficulty in decoupling mitogenicity and antiviral activity by mutagenesis and indicates that biological activity may require pi-pi stacking between the two aromatic amino acids 83 and 84.

Ten of the above H84 mutants were examined by NMR spectroscopy to establish structure (or chemical shift)-activity relationships. The different mutants yielded excellent overall spectral agreement, indicating that they all adopt a similar protein fold, and presented perturbations relative to the spectrum of the WT protein only for regions assigned to the third Greek Key (FIG. 6). Further analysis of these differences yielded an interesting trend for several residues; for residue A86, the signals observed in all the mutants fall roughly along a straight line. Similar behaviors, too, are observed for V87 and V88, though the magnitude of the change is smaller and more difficult to resolve due to spectral overlap. Furthermore, mutants with aromatic residues (H84F, H84W and H84Y) that can support pi-pi stacking between amino acids 83 and 84 and that have higher mitogenicity and anti-HIV activity (FIG. 6) also display A86 resonance clustering upfield along the line as compared to other mutants. A simple explanation that could account for these observations is that BanLec exists in rapid exchange between two states and that the mutations differentially shift the relative population of the two states, thus resulting in an apparent linear change in resonance position (Palmer, 2004 supra). A similar behavior has previously been observed with mutations in the context of modulating accessibility to protein sites that undergo phosphorylataton (Li et al., 2008 Nat Struct Mol Biol 15, 613-618).

The exchange process could influence a significant part of, or even the entire, third Greek Key with A86 acting as a reporter for the process, A86 is both strongly affected by it and still remote enough from the mutation site to not exhibit chemical shift modulation due to the change in the nature of residue 84. Residue 86, despite being close in the primary sequence is, according to the crystal structures, on the opposite side of the third Greek Key loop, making it a priori a good reporter of structural and dynamic changes and hence the capacity for mitogenicity. For V87 and V88, such trends are more difficult to discern, but clearly resonances cluster depending on whether aromatic or non-aromatic residues are used in the substitution. These two residues constitute the back part of the third Greek Key loop.

Thus, the results indicate that the mutants with aromatic residues present a more rigid loop due to the existence of pi-pi stacking between amino acids 83 and 84, and this could influence the conformational flexibility of the entire loop. On the other end, the loss of pi-pi stacking could push the system toward a different conformational state of the loop. The pi-stacked conformation could be biologically active (both mitogenic and with antiviral activity), whereas the second conformation would be less, or even not, active. Looking at individual chemical-shift signatures, the H84T mutant protein presents characteristics of an aromatic residue for A86, whereas the V87 and V88 signals cluster with non-aromatic residues. This indicates that the third Greek Key loop in the H84T mutant exhibits intermediate characteristics between typical aromatic and non-aromatic mutants, correlating with loss of mitogenicity, as for other non-aromatic mutants, while retaining antiviral activity, similar to an aromatic mutant.

TABLE 1

Comparison of the calorimetric and hemagglutination properties of WT and H84T BanLec

| | WT | H84T | Fold Change |
|---|---|---|---|
| methyl-α-mannoside ($K_a$, $mM^{-1}$) | 383 | 353 | 1.09 |
| mannobiose ($K_a$, $mM^{-1}$) | 300 | 227 | 1.32 |
| minimal agglutination concentration (μg/ml) | 3 | 487 | 162 |

TABLE 2

$IC_{50}$-values for 11 types of glycoclusters in binding assays with WT and H84T BanLec (in mM)*

| No. | Valency | $IC_{50}$ of WT (mM) | $IC_{50}$ of H84T (mM) | Fold Change |
|---|---|---|---|---|
| 1 | bi | 1 | 0.2 | 5 |
| 2 | bi | 0.5 | 0.08 | 6.3 |
| 3 | bi | 0.6 | 0.1 | 6 |
| 4 | tetra | 5 | 1.3 | 3.9 |
| 5 | tetra | 1.4 | 0.5 | 2.8 |
| 6 | hexa | 1.6 | 0.36 | 4.4 |
| 7 | octa | 0.04 | 0.02 | 2 |
| 8 | dodeca | 0.025 | 0.008 | 3.1 |
| 9 | bi | 4.5 | 2.1 | 2.1 |
| 10 | tri | 2.8 | 0.8 | 3.5 |
| 11 | tetra | 2.1 | 0.5 | 4.2 |

*Assays were run using a constant amount of neoglycoprotein (0.5 μg) for coating and 0.5/1 μg/ml labeled lectin (WT/mutant) in triplicates with up to six independent series with standard deviations not exceeding 14.2%; concentration values are normalized to mannose (cpds 1-8) and maltose (cpds 9-11); for the structures of the glycoclusters, please see FIG. 3A.

TABLE 3

Crystallography data collection and refinement statistics

| Data Collection | WT | H84T mutant | WT + 2man | H841 + 2man |
|---|---|---|---|---|
| Space Group | P2$_1$ | P2$_1$2$_1$2$_1$ | P2$_1$ | P2$_1$ |
| Unit Cell a, b, c (Å) | 50.510, 94.492, 63.443, =97.47 | 47.11, 63.22, 95.71 | 50.456, 94.708, 63.347, =97.5 | 50.613, 94.963, 63.054, =97.6 |
| Wavelength (Å) | 1.07820 | 0.97853 | 1.0781 | 1.0781 |
| Resolution (Å)$^1$ | 1.7 (1.73-1.70) | 1.6 (1.63-1.60) | 1.7 (1.73-1.70) | 1.55 (1.58-1.55) |
| Rsym (%)$^2$ | 6.2 (30.9) | 7.0 (47.2) | 4.5 (17.5) | 4.4 (19.6) |
| <I/sI>$^3$ | 20 (5) | 20 (3) | 20 (10) | 20 (10) |
| Completeness (%)$^4$ | 98.7 (96.9) | 100 (100) | 99.9 (99.3) | 99.9 (99.3) |
| Redundancy | 3.8 (3.6) | 7.1 (7.2) | 3.8 (3.6) | 3.7 (3.6) |
| Refinement | | | | |
| Resolution (Å) | 1.70 | 1.60 | 1.70 | 1.55 |
| R-Factor (%)$^5$ | 16.8 | 15.3 | 16.4 | 17.0 |
| Rfree (%)$^6$ | 19.8 | 17.8 | 18.7 | 19.1 |
| Protein Atoms | 4125 | 2045 | 4116 | 4147 |
| Water Molecules | 643 | 283 | 576 | 667 |
| Unique Reflections | 63876 | 38064 | 64884 | 85500 |
| R.m.s.d.$^7$ | | | | |
| Bonds | 0.010 | 0.015 | 0.010 | 0.010 |
| Angles | 1.07 | 1.522 | 1.10 | 1.10 |
| MolProbity Score$^8$ | 1.21 | 1.37 | 1.30 | 1.25 |
| Clash Score$^8$ | 3.18 | 3.81 | 3.83 | 3.09 |
| Z-Score$^9$ (A/B/C/D) chain | −0.41/−0.36/ −0.33/−0.41 | −0.27/−0.16 | −0.52/−0.33/ −0.28/−0.43 | −0.23/−0.12/ −0.17/−0.23 |

$^1$Statistics for highest resolution bin of reflections in parentheses.
$^2$R$_{sym}$ = Σ$_h$Σ$_j$ I I$_{hj}$ − <I$_h$> I/Σ$_h$Σ$_j$I$_{hj}$, where I$_{hj}$ is the intensity of observation j of reflection h and <I$_h$> is the mean intensity for multiply recorded reflections.
$^3$Intensity signal-to-noise ratio.
$^4$Completeness of the unique diffraction data.
$^5$R-factor = Σ$_h$ I IF$_o$I − IF$_c$I I/Σ$_h$IF$_o$I, where F$_o$ and F$_c$ are the observed and calculated structure factor amplitudes for reflection h.
$^6$R$_{free}$ is calculated against a 10% random sampling of the reflections that were removed before structure refinement.
$^7$Root mean square deviation of bond lengths and bond angles.
$^8$Chen et al. (2010) MolProbity: all-atom structure validation for macromolecular crystallography. Acta Cryst. D66: 12-21.
$^9$Kleywegt et al. (2004) "The Uppsala Electron-Density Server". Acta Cryst. D60, 2240-2249.

TABLE 4

Refinement statistics for mannose residues

| | | WT | | |
|---|---|---|---|---|
| Chain | CBS | Mannose Residue | RSR$^1$ | RSCC$^1$ |
| A | I | 501 | 0.173 | 0.882 |
|  | II | 601 | 0.139 | 0.907 |
| B | I | 501 | 0.083 | 0.945 |
|  |  | 502 | 0.146 | 0.855 |
|  | II | 601 | 0.136 | 0.901 |
| C | I | 501 | 0.187 | 0.885 |
|  |  | 502 | 0.490 | 0.693 |
|  | II | 601 | 0.134 | 0.908 |
| D | I | 501 | 0.070 | 0.969 |
|  |  | 502 | 0.127 | 0.885 |
|  | II | 601 | 0.144 | 0.909 |
| | | H84T | | |
| Chain | CBS | Mannose Residue | RSR | RSCC |
| A | I | 501 | 0.091 | 0.940 |
|  |  | 502 | 0.289 | 0.690 |
|  | II | 601 | 0.104 | 0.924 |
| B | I | 501 | 0.061 | 0.974 |
|  |  | 502 | 0.083 | 0.948 |
|  | II | 601 | 0.074 | 0.956 |
|  |  | 602 | 0.287 | 0.839 |
| C | I | 501 | 0.086 | 0.965 |
|  |  | 502 | 0.120 | 0.957 |
|  | II | 601 | 0.101 | 0.932 |
| D | I | 501 | 0.051 | 0.984 |
|  |  | 502 | 0.071 | 0.954 |
|  | II | 601 | 0.074 | 0.948 |

$^1$Kleywegt et al. (2004) "The Uppsala Electron-Density Server". Acta Cryst. D60, 2240-2249.

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure which are obvious to those skilled in the relevant fields are intended to be within the scope of the following claims.

The invention claimed is:

1. A composition comprising a variant lectin polypeptide comprising at least one mutation that disrupts pi-pi aromatic stacking, wherein said variant lectin polypeptide exhibits antiviral or antimicrobial activity, and wherein said lectin polypeptide exhibits reduced mitogenic activity relative to a wild type lectin polypeptide, wherein said variant lectin is not a banana lectin, and wherein said variant lectin polypeptide is not the polypeptide of SEQ ID NO:9 or 2.

2. The composition of claim 1, wherein said variant lectin polypeptide is selected from the group consisting of a variant of *Malus domestica* agglutinin alpha chain-like; a variant of *Oryza sativa* Indica Group hypothetical protein OsI_37872; a variant of *Theobroma cacao* Mannose-binding lectin superfamily protein; a variant of *Cycas rumphii* jacalin-related lectin; a variant of *Cycas revoluta* lectin; Setari 4714 *italica* mannose/glucose-specific lectin-like isoform X1; a variant of *Setaria* 4714 *italica* mannose/glucose-specific lectin-like isoform X2; and a variant of *Oryza* from rice brachyantha disease resistance protein RPM1-like.

3. The composition of claim 2, wherein said variant lectin is selected from a lectin comprising mutations at positions 81 or 82 of SEQ ID NO:3; positions 74 or 75 of SEQ ID NO:4; positions 74 or 75 of SEQ ID NO:5; positions 84 or 85 of SEQ ID NO:6; positions 84 or 85 of SEQ ID NO:7; and 81 or 82 of SEQ ID NO:8.

4. The composition of claim 3, wherein said amino acid is mutated to a non-aromatic amino acid.

5. The composition of claim 1, wherein said composition is an anti-viral, anti-microbial, anti-fungal, and/or anti-parasitic pharmaceutical composition.

6. The compositions of claim 1, wherein said composition treats infection by microorganisms presenting surface mannose.

7. The composition of claim 1, wherein said composition treats infection by a virus selected from HIV, corona virus and influenza virus.

8. A method of treating infection by a microorganism comprising administering a composition of claim 1 to a subject at risk of infection, suspected of having an infection, or diagnosed with infection by a microorganism.

9. The method of claim 8, wherein said composition is administered topically.

10. The method of claim 8, wherein said composition treats said infection systemically.

11. The method of claim 8, wherein said infection is by a microorganism comprising surface mannose.

12. The method of claim 8, wherein said microorganism is a virus, bacteria, parasite, or fungus.

13. The method of claim 12, wherein said virus is selected from HIV, influenza, and corona virus.

14. A medical device or product comprising the composition of claim 1.

15. The product of claim 14, wherein said product is a condom.

* * * * *